(12) United States Patent
Chandler

(10) Patent No.: US 9,782,457 B2
(45) Date of Patent: Oct. 10, 2017

(54) FLOWABLE FORMULATIONS FOR TISSUE REPAIR AND REGENERATION

(71) Applicant: Tissue Repair Company, San Diego, CA (US)

(72) Inventor: Lois Chandler, San Diego, CA (US)

(73) Assignee: TISSUE REPAIR COMPANY, San Diego, CA (US)

(*) Notice: Subject to any disclaimer, the term of this patent is extended or adjusted under 35 U.S.C. 154(b) by 0 days.

(21) Appl. No.: 13/648,255

(22) Filed: Oct. 9, 2012

(65) Prior Publication Data
US 2013/0096064 A1 Apr. 18, 2013

Related U.S. Application Data

(60) Provisional application No. 61/545,106, filed on Oct. 7, 2011.

(51) Int. Cl.
| | |
|---|---|
| *A61K 38/39* | (2006.01) |
| *A61K 45/06* | (2006.01) |
| *A61K 36/39* | (2006.01) |
| *A61K 9/00* | (2006.01) |
| *A61L 27/24* | (2006.01) |
| *A61L 26/00* | (2006.01) |

(52) U.S. Cl.
CPC .......... *A61K 38/39* (2013.01); *A61K 9/0014* (2013.01); *A61K 36/39* (2013.01); *A61K 45/06* (2013.01); *A61L 26/0033* (2013.01); *A61L 26/0066* (2013.01); *A61L 27/24* (2013.01); *A61L 2400/06* (2013.01); *A61L 2430/34* (2013.01)

(58) Field of Classification Search
CPC ........ A61K 38/39; A61K 45/06; A61K 36/39; A61K 9/0014; A61K 2300/00; A61L 26/0033; A61L 27/24; A61L 26/0066; A61L 2400/06; A61L 2430/34
See application file for complete search history.

(56) References Cited

U.S. PATENT DOCUMENTS

| | | | | |
|---|---|---|---|---|
| 4,440,750 A | * | 4/1984 | Glowacki et al. | 424/572 |
| 4,745,098 A | * | 5/1988 | Michaeli | A61K 38/39 |
| | | | | 514/13.7 |
| 4,913,904 A | * | 4/1990 | Fyodorov et al. | 424/427 |
| 5,425,770 A | * | 6/1995 | Piez | A61L 27/46 |
| | | | | 264/101 |
| 5,750,146 A | * | 5/1998 | Jones et al. | 424/484 |

OTHER PUBLICATIONS

Kato, Mechanism of collagen-induced release of 5-HT, PDGF-AB and sCD40L from human platelets: Role of HSP27 phosphorylation via p44/p42 MAPK, Thrombosis Research 126:39-43, 2010.*
Ruszczak, Collagen as a carrier for on-site delivery of antibacterial drugs, Advanced Drug Delivery Reviews 55:1679-1698, 2003.*
Van Der Rest et al, Collagen family od proteins, FASEB J., 1991, 5, pages 2814-2823.*
Definition of Sol, from http://www.merriam-webster.com/dictionary/sol, pp. 1-4, accessed Feb. 8, 2016.*
Definition of colloidal suspension, from http://www.thefreedictionary.com/colloidal+suspension, p. 1, accessed Feb. 8, 2016.*
Sonnemann et al, Wound Repair: Toward Understanding and Integration of Single-Cell and Multicellular Wound Responses, Annu. Rev. Cell Dev. Biol., 2011, 27, pp. 237-263.*
Zielins et al, Emerging drugs for the treatment of wound healing, Expert Opin. Emerging Drugs, 2015, 20, pp. 235-246.*
Fitzgerald et al, Collagen in Wound Healing: Are We Onto Something New or Just Repeating the Past?, The Foot and Ankle Online Journal, 2009, 2, pp. 1-5.*

* cited by examiner

*Primary Examiner* — Julie Ha
*Assistant Examiner* — Li Ni Komatsu
(74) *Attorney, Agent, or Firm* — VLP Law Group, LLP

(57) ABSTRACT

A formulation and method are provided for treating wounds by promoting healing and tissue repair and/or regeneration therein. The formulation is a topically administrable selectively flowable colloidal suspension that contains a tropocollagen, at least one adjuvant effective to enhance the capability of the formulation or the tropocollagen to promote tissue repair and regeneration following topical administration to a wound, and a physiologically acceptable carrier or excipient. At least 50% of the tropocollagen is composed of renatured tropocollagen, generally renatured atelopeptide tropocollagen. Methods for using the formulation to heal a wound and effect tissue repair and/or regeneration therein are also provided.

23 Claims, No Drawings

FLOWABLE FORMULATIONS FOR TISSUE REPAIR AND REGENERATION

CROSS-REFERENCE TO RELATED APPLICATIONS

This patent application claims the benefit of U.S. Provisional Application 61/545,106 filed Oct. 7, 2011.

TECHNICAL FIELD

The present invention relates generally to flowable tropocollagen formulations and uses of such formulations for promoting healing and tissue repair and/or regeneration in wounds induced by, for example, trauma or injury, a disease state, bed sores or other pressure ulcers, or surgery.

BACKGROUND OF THE INVENTION

The number of wounds and market for products promoting wound healing is substantial and rising. Over 110 million iatrogenic wounds, wounds that are either induced or caused by a medical procedure, are created every year, while an estimated 20 million patients seek medical attention for traumatic wounds.

Difficult to heal and chronic wounds, including pressure ulcers, venous ulcers, and diabetic ulcers are growing in incidence every year due to the aging of the population. Approximately 8.5 million patients world wide suffer from pressure ulcers, an estimated 12.5 million patients suffer from venous ulcers, and approximately 13.5 million patients suffer from diabetic ulcers. The associated morbidities and mortalities are also very significant and increasing. For example, non-healing diabetic ulcers not only affect patient mobility but are a leading cause of amputations in the U.S. and many other industrialized countries. Approximately 50% of such amputees die from associated co-morbidities within three years of amputation.

In the case of the diabetic foot ulcers, the current Standard of Care (SOC) includes surgical debridement, moist dressing changes, and off-loading. Currently available secondary interventions include living skin equivalents, hyperbaric oxygen, negative pressure devices, antibiotics for infection, specialized dressings, or a topical gel containing growth factors or collagen. Such secondary interventions provide moderate improvement over the SOC and can be expensive, time consuming, and/or difficult to use. In addition, despite these interventions, many wounds do not heal and may worsen to the point where an amputation becomes necessary. There remains a need for an easy to use and effective treatment of these and other wounds.

The present invention relates generally to formulations of atelopeptide tropocollagen matrices and uses of such formulations for promoting healing and tissue repair and/or regeneration in wounds induced by, for example, trauma or injury, a disease state, bed sores, or surgery.

DESCRIPTION OF THE RELATED ART

Various collagen formulations and uses thereof have been described in the art, see, e.g. U.S. Pat. Nos. 3,034,852; 3,121,049; 3,131,130; 3,314,861; 3,530,037; 3,949,073; 4,140,537, 2,920,000; 2,934,446-7; 3,014,024; 3,562,820; 3,563,228; 4,331,766, 3,491,760, 4,760,131; 4,808,570; 4,745,098; 4,950,483; 7,993,679; 5,219,576; 5,110,604; 5,024,841; and 5,128,136, Brett D, A Review of Collagen and Collagen-based Wound Dressings, Wounds 20(12), (2008); Li W. et al, Mechanism of Human Dermal Fibroblast Migration Driven by Type I Collagen and Platelet-derived Growth Factor-BB, Mol. Biol. Cell 15:294-309 (2004); Rangaraj A et al., Role of Collagen in Wound Management, Wounds UK 7(2): 54-63 (2011); Sai P K and Babu, Collagen Based Dressings—a Review, Burns 26:54-62 (2000); Shoulders M D and Raines R T, Collagen Structure and Stability, Ann Rev. Biochem. 78:929-958 (2009); Sylvester M F et al, Collagen Banded Fibril Structure and the Collagen-Platelet Reaction, Thromb. Res. 55: 135-148 (1989); and references cited therein, those and all other references referred to in this application being expressly incorporated by reference.

BRIEF SUMMARY OF THE INVENTION

The present invention relates generally to formulations of atelopeptide tropocollagen and uses of such formulations for promoting healing and tissue repair and/or regeneration in wounds induced by, for example, trauma or injury, a disease state, or iatrogenic wounds. Various terms used herein are defined below.

In a preferred embodiment the formulation comprises tropocollagen, at least one adjuvant, and a physiologically acceptable carrier. The formulation preferably comprises a selectively flowable colloidal suspension or colloid. In preferred embodiment the formulation comprises a selectively flowable sol. In an alternative embodiment the formulation comprises a selectively flowable gel. In another embodiment the formulation comprises an emulsion.

The tropocollagen as used in the formulation is preferably an atelopeptide tropocollagen in which the terminal peptides have been removed, e.g. by enzyme degradation such as pepsin degradation as illustrated below. The tropocollagen is preferably renatured for use in the final formulation. In one embodiment at least 50% of the tropocollagen is renatured. In a preferred embodiment at least 75% percent of the tropocollagen is renatured. In a more preferred embodiment at least 90% of the collagen is renatured. In an exemplary embodiment at least 95% of the tropocollagen is renatured. In a preferred embodiment, the tropocollagen is capable of promoting the release of PDGF by platelets. The tropocollagen is preferably type I bovine collagen.

The formulation, in a preferred embodiment has a neutral pH. In one embodiment the formulation has a pH of 6 to 9. In a more preferred embodiment the formulation has a pH of 7 to 8.

In a preferred embodiment the formulation exhibits sufficient flow at a temperature of approximately 15° C. to be extruded through a syringe, canula, applicator tip, or any device used to deliver a colloid to a wound. The formulation in a preferred embodiment exhibits sufficient flow at about 20° to 25° C. to fill the recesses or tunnels of a wound to which it is applied.

In a preferred embodiment at least one adjuvant in the formulation is a structural modulator. In a more preferred embodiment the structural modulator is a tropocollagen stabilizer. In one embodiment the tropocollagen stabilizer is a polyol. In a preferred embodiment at least one structural modulator is a formulation modulator.

In one preferred embodiment at least one adjuvant is an enhancer. In another preferred embodiment at least one enhancer is an antimicrobial agent. In another preferred embodiment at least one antimicrobial agent is an alcohol. In another preferred embodiment at least one enhancer for use in the formulation is an MMP inhibitor. In a more preferred embodiment, at least one MMP inhibitor is a zinc chelator.

In preferred embodiments, the formulation is sterile.

The present invention also provides the use of the formulation and methods of use of the formulation. In one embodiment the formulation is for use in tissue repair. In another embodiment the formulation is for use in tissue regeneration. In a preferred embodiment the formulation is for use in healing a wound. In a preferred embodiment of the wound is a chronic wound. In a more preferred embodiment the wound is a diabetic ulcer. In a preferred embodiment the formulation is applied to the wound. In a more preferred embodiment the formulation is applied to the wound after surgical debridement. In a still more preferred embodiment a new application of the formulation is not administered to the wound for at least one week after the original application. In a most preferred embodiment a new application of the formulation is not administered to the wound for at least two weeks after the original application.

The present invention also provides for a device comprising a reservoir containing the formulation. In one embodiment the device comprises a syringe. In a preferred embodiment the device comprises an applicator tip through which the formulation can be extruded. In a preferred invention the formulation can be extruded from the device by the application of hand pressure. In a more preferred embodiment the applicator tip comprises a flexible tube that allows the device to be held at various angels relative to the angel of the extrusion of the formulation. In a most preferred embodiment the applicator tip is intended for a single use.

The present invention further provides for a kit comprising the device and instructions for use.

The present invention further provides a means to produce the formulation.

Exemplary embodiments of the invention include as follows:

1. A formulation comprising (i) a tropocollagen, (ii) at least one adjuvant, and (iii) a physiologically acceptable excipient, wherein said formulation is a selectively flowable colloid.
2. A formulation according to embodiment 1, wherein the tropocollagen is an atelopeptide tropocollagen.
3. A formulation according to any of the preceding embodiments, wherein the tropocollagen is renatured tropocollagen.
4. A formulation according to any of the preceding embodiments, wherein the tropocollagen is non-cross-linked tropocollagen.
5. A formulation according to any of the preceding embodiments, wherein the colloid is a sol.
6. A formulation according to any of the preceding embodiments, wherein the tropocollagen is non-aggregated and is dispersed within the excipient to form a homogeneous dispersion.
7. A formulation according to any of the preceding embodiments, wherein the formulation has a neutral pH.
8. A formulation according to any of the preceding embodiments, wherein the formulation at a temperature of approximately 15° C. exhibits sufficient flow to be extruded through a syringe, cannula, applicator tip, or any device used to deliver a colloid to a wound.
9. A formulation according any of the preceding embodiments, wherein at a temperature of approximately 15° C. the formulation exhibits sufficient flow to be extruded from syringe into a recess or tunnel of a wound.
10. A formulation according to any of the preceding embodiments, wherein at least one adjuvant is a structural modulator.
11. A formulation according to embodiment 10, wherein the structural modulator is a tropocollagen stabilizer.
12. A formulation according to embodiment 11, wherein the tropocollagen stabilizer is a polyol.
13. A formulation according to embodiment 10, wherein the structural modulator is a formulation modulator.
14. A formulation according to any of the preceding embodiments, wherein the tropocollagen is capable of promoting the release of PDGF by platelets.
15. A formulation according to any of the preceding embodiments, wherein at least one adjuvant is an enhancer.
16. A formulation according to embodiment 15, wherein the enhancer is an antimicrobial agent.
17. A formulation according to embodiment 16, wherein the antimicrobial agent is an alcohol.
18. A formulation according to embodiment 15, wherein the enhancer is an MMP inhibitor.
19. A formulation according to embodiment 18, wherein the MMP inhibitor is a zinc chelating agent.
20. A formulation according to any of the preceding embodiments, wherein the formulation is sterile.
21. A formulation according to any of the preceding embodiments, wherein the tropocollagen is bovine type I tropocollagen.
22. A formulation according to any of the preceding embodiments, wherein the tropocollagen is non-lyophilized tropocollagen.
23. A formulation according to any of the preceding embodiments, wherein the formulation does not comprise PDGF or a gene encoding PDGF.
24. A use of a selectively flowable colloid formulation comprising (i) a tropocollagen, (ii) at least one adjuvant, and (iii) a physiologically acceptable excipient, for treating a wound.
25. A use according to embodiment 24, wherein the tropocollagen is an atelopeptide tropocollagen.
26. A use according to embodiment 24 or 25, wherein the tropocollagen is renatured tropocollagen.
27. A use according to any of embodiments 24-26, wherein the tropocollagen is non-cross-linked tropocollagen.
28. A use according to any of embodiments 24-27, wherein the colloid is a sol.
29. A use according to any of embodiments 24-28, wherein the tropocollagen is non-aggregated and is dispersed within the excipient to form a homogeneous dispersion.
30. A use according to any of embodiments 24-29, wherein the formulation has a neutral pH.
31. A use according to any of embodiments 24-30, wherein the formulation at a temperature of approximately 15° C. exhibits sufficient flow to be extruded through a syringe, cannula, applicator tip, or any device used to deliver a colloid to a wound.
32. A use according any of embodiments 24-31, wherein at a temperature of approximately 15° C. the formulation exhibits sufficient flow to be extruded from syringe into a recess or tunnel of a wound.
33. A use according to any of embodiments 24-32, wherein at least one adjuvant is a structural modulator.
34. A use according to embodiment 33, wherein the structural modulator is a tropocollagen stabilizer.
35. A use according to embodiment 34, wherein the tropocollagen stabilizer is a polyol.
36. A use according to embodiment 33, wherein the structural modulator is a formulation modulator.
37. A use according to any of embodiments 24-36, wherein the tropocollagen is capable of promoting the release of PDGF by platelets.
38. A use according to any of embodiments 24-37, wherein at least one adjuvant is an enhancer.

39. A use according to embodiment 38, wherein the enhancer is an antimicrobial agent.
40. A use according to embodiment 39, wherein the antimicrobial agent is an alcohol.
41. A use according to embodiment 38, wherein the enhancer is an MMP inhibitor.
42. A use according to embodiment 41, wherein the MMP inhibitor is a zinc chelating agent.
43. A use according to any of embodiments 24-42, wherein the formulation is sterile.
44. A use according to any of embodiments 24-43, wherein the tropocollagen is bovine type I tropocollagen.
45. A use according to any of embodiments 24-44, wherein the tropocollagen is non-lyophilized tropocollagen.
46. A use according to any of embodiments 24-45, wherein the formulation does not comprise PDGF or a gene encoding PDGF.
47. A use according to any of embodiments 24-46, wherein the wound is a traumatic injury wound.
48. A use according to any of embodiments 24-47, wherein the wound is associated with a diseased state.
49. A use according to any of embodiments 24-48, wherein the wound is an iatrogenic wound.
50. A use according to any of embodiments 24-49, wherein the wound is a soft tissue wound.
51. A use according to any of embodiments 24-50, wherein the wound is a chronic wound.
52. A use according to any of embodiments 24-51, wherein the wound is a diabetic foot ulcer.
53. A method of treating a wound comprising applying to the wound a selectively flowable formulation comprising (i) a tropocollagen, (ii) at least one adjuvant, and (iii) a physiologically acceptable excipient.
54. A method according to embodiment 53, wherein the tropocollagen is an atelopeptide tropocollagen.
55. A method according to embodiment 53 or 54, wherein the tropocollagen is renatured tropocollagen.
56. A method according to any of embodiments 53-55, wherein the tropocollagen is non-cross-linked tropocollagen.
57. A method according to any of embodiments 53-56, wherein the colloid is a sol.
58. A method according to any of embodiments 53-57, wherein the tropocollagen is non-aggregated and is dispersed within the excipient to form a homogeneous dispersion.
59. A method according to any of embodiments 53-58, wherein the formulation has a neutral pH.
60. A method according to any of embodiments 53-59, wherein the formulation at a temperature of approximately 15° C. exhibits sufficient flow to be extruded through a syringe, cannula, applicator tip, or any device method to deliver a colloid to a wound.
61. A method according any of embodiments 53-60, wherein at a temperature of approximately 15° C. the formulation exhibits sufficient flow to be extruded from syringe into a recess or tunnel of a wound.
62. A method according to any of embodiments 53-61, wherein at least one adjuvant is a structural modulator.
63. A method according to embodiment 62, wherein the structural modulator is a tropocollagen stabilizer.
64. A method according to embodiment 63, wherein the tropocollagen stabilizer is a polyol.
65. A method according to embodiment 62, wherein the structural modulator is a formulation modulator.
66. A method according to any of embodiments 53-65, wherein the tropocollagen is capable of promoting the release of PDGF by platelets.
67. A method according to any of embodiments 53-66, wherein at least one adjuvant is an enhancer.
68. A method according to embodiment 67, wherein the enhancer is an antimicrobial agent.
69. A method according to embodiment 68, wherein the antimicrobial agent is an alcohol.
70. A method according to embodiment 67, wherein the enhancer is an MMP inhibitor.
71. A method according to embodiment 70, wherein the MMP inhibitor is a zinc chelating agent.
72. A method according to any of embodiments 53-71, wherein the formulation is sterile.
73. A method according to any of embodiments 53-72, wherein the tropocollagen is bovine type I tropocollagen.
74. A method according to any of embodiments 53-73, wherein the tropocollagen is non-lyophilized tropocollagen.
75. A method according to any of embodiments 53-74, wherein the formulation does not comprise PDGF or a gene encoding PDGF.
76. A method according to any of embodiments 53-75, wherein the wound is a traumatic injury wound.
77. A method according to any of embodiments 53-76, wherein the wound is associated with a diseased state.
78. A method according to any of embodiments 53-77, wherein the wound is an iatrogenic wound.
79. A method according to any of embodiments 53-78, wherein the wound is a soft tissue wound.
80. A method according to any of embodiments 53-79, wherein the wound is a chronic wound.
81. A method according to any of embodiments 53-80, wherein the wound is a diabetic foot ulcer
82. A method according to any of embodiments 53-81, further comprising the step of re-application of the formulation to the wound.
83. A method according to embodiment 82, wherein a second application of the formulation is made approximately one week following the initial application.
84. A method according to embodiment 82, wherein a third application of the formulation is made approximately one week following the second application.
85. A device comprising a formulation according to any one of embodiments 1-23.
86. A device of embodiment 85, wherein the device is a syringe barrel containing the formulation.
87. A device of embodiment 86, wherein the syringe barrel is adapted for receiving an applicator tip suitable for application to a wound.
88. A device of embodiment 86, wherein the syringe barrel comprises a reservoir containing the formulation, and wherein the reservoir is operably linked to an applicator tip suitable for application to a wound.
89. A device of embodiment 85, wherein the syringe barrel is operably joined to an applicator tip suitable for application to a wound.
90. A device of embodiment 89, wherein the applicator tip comprises a flexible tube.
91. A kit comprising a device of any one of embodiments 85-90, further comprising instructions for use of the device in the treatment of a wound.
92. A method of preparing a formulation according to any one of embodiments 1-23, comprising the following steps: (i) a collagen grindate is denatured and solubilized in a first solution resulting in a solubilized collagen in solution, (ii) a renaturing agent is added to the solubilized collagen in solution resulting in the formation of renatured tropocollagen, (iii) the renatured tropocollagen is dispersed in a pharmaceutically acceptable excipient.

93. A method of embodiment 92, wherein the first solution is an acidic solution comprising pepsin.

94. A method of embodiment 93, wherein the renaturing agent is a base added to the solution to increase the pH to neutral range and the solution is mixed to allow renatured tropocollagen to form.

95. A method of embodiment 94, wherein the renatured tropocollagen is isolated from the solution by centrifugation before being dispersed in a pharmaceutically acceptable excipient 96. A method of embodiment 94, wherein the collagen grindate is obtained from bovine hides that have been soaked in an acidic solution.

97. A method of any of embodiments 92-96, wherein the collagen in solution is passed through a sterile filter to remove contaminants and all subsequent steps are performed aseptically.

98. A method of any of embodiments 92-97, wherein the tropocollagen formulation is approximately 2.6% bovine atelopeptide tropocollagen in the form of a selectively flowable sol.

99. A method of any of embodiments 92-98, further comprising sterile fill of devices comprising a reservoir adapted to contain the tropocollagen formulation and maintain it in sterile form.

100. A method of embodiment 99, wherein the device is a syringe barrel.

DETAILED DESCRIPTION OF THE INVENTION

Various preferred aspects of the present invention are described in further detail below. Prior to further setting forth additional details regarding the invention, it may be helpful to an understanding thereof to set forth definitions of certain terms that will be used hereinafter.

An "adjuvant" as used herein generally refers to any agent that modulates or enhances the function of the formulation or tropocollagen to promote tissue repair and regeneration in wounds or other tissue injuries.

An "antimicrobial agent" as used herein generally refers to any agent that reduces or inhibits the reproduction and/or proliferation of microorganisms in a wound or other site of tissue injury that is suitable for use in a human or other mammal.

A "cytokine" is any agent that alters a cellular function or activity in a cell exposed to the agent. Preferred classes of cytokines in the present invention include signaling proteins that promote tissue repair and regeneration, including growth factors and other agents that promote re-epithelialization, angiogenesis, matrix production, and scar formation in wounds.

A "colloid" as used herein generally refers to a system in which one substance has another substance dispersed within it.

A "formulation modulator" generally refers to any agent that modulates the viscosity, inter-collagen interactions, or other physiochemical properties of tropocollagen formulations.

A "structural modulator" as referred to herein generally refers to any agent that modulates the structure of the tropocollagen or the formulation.

A "tropocollagen stabilizer" generally refers to any agent that promotes the stability of tropocollagen, allows for its extended storage, or otherwise under refrigeration or room temperatures minimizes or inhibits the degradation of tropocollagen.

An "enhancer" as used herein generally refers to any agent that improves, potentiates, or otherwise enhances the ability of tropocollagen matrices to promote tissue repair and regeneration.

A "repair cell," as used herein, generally refers to any cell that is stimulated to migrate and proliferate in response to tissue injury. Repair cells are a component of the wound healing response. Such cells include macrophages, lymphocytes, epithelial cells, fibroblasts, capillary endothelial cells, capillary pericytes, mast cells, megakaryocytes, keratinocytes, smooth muscle cells, mononuclear inflammatory cells, segmented inflammatory cells, granulation tissue cells, tissue specific cells and their precursors, including but not limited to hepatocytes, cardiac myocytes, renal tubular cells, type II pneumocytes, keratinocytes, intestinal cells, gastric cells, chondroblasts, osteoblasts, and the like.

A "wound site," as used herein, generally refers to any location in the host that arises from traumatic tissue injury, from a disease state, or from tissue damage either induced by, or resulting from, medical procedures including injection or suturing or similar procedures.

"Cellular infiltration," as used herein, generally refers to cell migration in reference to a tropocollagen matrix. Cellular infiltration encompasses cell migration into and along the interior surface of a tropocollagen matrix. Cellular infiltration also includes cell migration across a permeable tropocollagen matrix.

A "gel" is a formulation intermediate between a solid and a free-flowing liquid.

A "tropocollagen" as used herein generally refers to a protein macromolecule comprised of three peptides ($\alpha$-chains) bound together via hydrogen bonds into a triple helix structure as well as renatured complexes thereof (i.e. microfibrils, fibrils, and fibers). Such "renatured tropocollagen" as used herein generally refers to tropocollagen that has been denatured and then renatured, for example, denatured in an acidic solution and then circulated in a neutral solution to allow the triple helix tropocollagen macromolecules to reform into renatured complexes. The term "atelopeptide tropocollagen" generally refers to the basic tropocollagen macromolecule or renatured tropocollagen, in each case with the terminal or end peptides predominately removed; preferably at least 95% removed, more preferably greater than 99% removed.

A "selectively flowable colloid" as used herein generally refers to a colloid that exhibits flow at certain temperatures and/or under certain applied pressures.

A "therapeutic protein" generally refers to any peptide, polypeptide, or protein that has the capacity to promote wound healing, tissue repair, or tissue regeneration. A therapeutic protein also includes any other peptide, polypeptide, or protein that treats, prevents, or lessens the symptoms or prognosis of any clinical disease, disorder or related biological manifestation.

An "iatrogenic wound" generally refers to a wound that is either induced by, or results from a medical procedure (e.g., injection, incision, puncture, osteotomy, excision, etc.).

The term "physiologically acceptable excipient" means an agent which is utilized in the formulation of a pharmaceutical agent as a pharmaceutical formulation, which is not deleterious to the host to which the formulation will be administered, and which does not substantially affect the pharmaceutical activity of the pharmaceutical agent with which it is formulated.

The term "aqueous solution" as used herein generally refers to solutions containing water (including deuterated water), preferably distilled water, and "saline solutions" (defined below), and which solutions may be pH adjusted with hydrochloric acid or sodium hydroxide, as may be necessary or desirable to stabilize or facilitate solubilization of the tropocollagen formulations of the present invention.

The term "saline solution" as used herein generally refers to solutions containing approximately 0.9% sodium chloride solubilized in water (including deuterated water), preferably distilled water, may be pH adjusted with hydrochloric acid or sodium hydroxide as may be necessary or desirable to stabilize or facilitate solubilization of the tropocollagen formulation of the present invention.

The pharmaceutical compositions and formulations of the invention are applicable to a wide variety of clinical diseases or pathological situations involving a wound. Wounds may arise from traumatic injury, from a disease state, or from tissue damage either induced by, or resulting from, a medical procedure. Illustrative wounds include diabetic foot ulcers and other wounds such as partial and full-thickness dermal wounds, pressure ulcers, venous ulcers, chronic vascular ulcers, tunneled/undermined wounds, surgical wounds (donor sites/grafts, post-Moh's surgery, post-laser surgery, podiatric, wound dehiscence), trauma wounds (abrasions, lacerations, second-degree burns and skin tears) and draining wounds. Wounds that may benefit from the application of the invention include, for example, diabetic ulcers, pressure ulcers, venous statis ulcers, arterial ulcers, surgical wounds, or high-energy trauma wounds. The compositions may also be of use in treating wounds that heal slowly, wounds that do not respond to existing therapies (e.g., chronic wounds) and in patients with impaired healing capacity resulting from, for example, diabetes and aging. In certain embodiments treatment methods of the invention are also useful when the clinical goal is to block a disease process, thereby allowing natural tissue healing to take place.

Wound healing is usually a coordinated, stereotyped sequence of events that includes (a) tissue disruption and loss of normal tissue architecture; (b) cell necrosis and hemorrhage; hemostasis (clot formation); (c) infiltration of segmented and mononuclear inflammatory cells, with vascular congestion and tissue edema; (d) dissolution of the clot as well as damaged cells and tissues by mononuclear cells (macrophages) (e) formation of granulation tissue (fibroplasia and angiogenesis); (f) regeneration of original tissue. This sequence of cellular events has been observed in wounds from all tissues and organs generated in a large number of mammalian species (Gailet et al., Curr. Opin. Cell. Biol. 6:717-725, 1994). Therefore, the cellular sequence described above is a nearly universal aspect of the repair of most mammalian tissues.

In certain formulations of the formulations of the invention, it is believed that repair cells involved in the wound healing process can be induced to proliferate and migrate to the site of tissue injury and infiltrate the applied tropocollagen formulation.

In one aspect of the invention, the formulation comprises tropocollagen colloids for use in administering or implanting onto or into a wound site. Administration of the formulation is performed by applying the formulation to the surface of the wound. Such administration can be accomplished by the means of an applicator as described herein. After the formulation is applied to the wound, cellular infiltration may occur as repair cells migrate into the applied tropocollagen formulation, such cells may express growth factors and provide a therapeutic effect to the tissue containing the tropocollagen formulation.

In a preferred embodiment the formulation will be comprised of 0.01 to 10% tropocollagen. In a more preferred embodiment the formulation will comprise approximately about 2.6% tropocollagen.

In certain embodiments, the formulation has sufficient surface area and exposure to nutrients such that cellular ingrowth and differentiation can occur prior to or concurrent to the ingrowth of blood vessels. After implantation, the formulation can allow for diffusion of nutrients and waste products and for continued blood vessel ingrowth as cell proliferation occurs. The organization of the growing tissue may be regulated by the microstructure of the matrix. Specific pore sizes and structures may be utilized to control the pattern and extent of fibrovascular tissue ingrowth from the host. Accordingly, cells may be seeded in the matrix before implantation. The organization of the seeded cells may also be guided. The surface geometry and chemistry of the matrix may be regulated to control the adhesion, organization, and function of seeded cells or in growing host cells.

The formulation will preferably have all the features commonly associated with being "biocompatible," in that it is in a form that does not produce an adverse, allergic or other untoward reaction when administered to a mammalian subject. The formulation will preferably be tailored according to the particular circumstances and the site of the wound that is to be treated. Physical and chemical characteristics, such as, e.g., biocompatibility, biodegradability, strength, rigidity, interface properties and even cosmetic appearance may be considered in choosing a formulation, as is well known to those of skill in the art. Appropriate formulations will preferably provide for matrix stability during storage and, following administration, also act as an in situ scaffolding through which mammalian repair cells may migrate.

Topical treatments for wounds and neuropathic ulcers containing collagen are known in the art. Such compositions typically contain lyophilized or hydrolyzed collagen, usually ground up into a powder and suspended in a saline fluid. Both hydrolyzation and lyophilization are known to break the hydrogen bonds supporting the secondary structure of proteins. When the hydrogen bonds are broken, the α-chains forming the secondary structure of the protein separate forming peptide fragments and single helix coils. The present invention comprises renatured tropocollagen. Preferably at least 50% of the collagen in the formulation is renatured tropocollagen. More preferably at least 75% of the collagen in the formulation is renatured tropocollagen. Still more preferably at least 90% of the collagen in the formulation is renatured tropocollagen. Most preferably at least 95% of the collagen in the formulation is renatured tropocollagen.

In a preferred embodiment the renatured tropocollagen is in the form of renatured complexes capable of promoting the activation of platelets to release PDGF, which in turn can stimulate the migration of macrophages and fibroblasts into the matrix and promote endogenous collagen and proteoglycan synthesis. Such preferred renatured complexes of the present invention have been shown to increase the activation of platelets to release PDGF by at least 50%. In a preferred embodiment the complexes increase the release of platelets by at least 100%. In a more preferred embodiment the complexes increases the release of platelets by at least 200%.

The formulations of the present invention preferably comprise tropocollagens that are not cross-linked, i.e. covalently linked to each other. "Cross-linked" as used herein generally refers to intra-collagen reactions wherein the tropocollagen macromolecules become bonded to other tropocollagen macromolecules to form aggregates. Preferably at least 75% of the tropocollagen is not cross-linked. More preferably at least 85% of the tropocollagen is not cross-linked. More preferably at least 90% of the tropocollagen is not cross linked. Most preferably at least 95% of the tropocollagen is not cross-linked.

In one embodiment the formulation is a selectively flowable colloidal suspension or a colloid. A preferred class of selectively flowable colloid is a tropocollagen sol in which non-cross-linked tropocollagen is dispersed in a liquid phase. An alternative colloid is a gel. Another alternative colloid is an emulsion. In a preferred embodiment, the formulation can be stored in a syringe and extruded through a canula, applicator tip, or any device or method used to deliver a colloid to a wound. The flowability of certain formulations will also preferably be high enough to fill a wound as well as any recesses or tunnels in or around the wound. The viscosity of certain formulations will preferably be high enough that it will not drip or flow off of the wound once applied.

In a preferred embodiment the formulation is sufficiently flowable at a temperature of approximately 15° C. to be extruded through a canula, applicator tip, or any device or method used to deliver a colloid to a wound. In a preferred embodiment, at a temperature of approximately 15° C., the formulation is sufficiently flowable to be readily spread across a wound and to fill recesses or tunnels of a wound, which may be aided by applications adapted to the nature and type of wound being treated.

In a preferred embodiment the formulation includes an adjuvant. An "adjuvant" as used herein generally refers to any agent that modulates or enhances the function of the formulation or tropocollagen to promote tissue repair and regeneration in wounds or other tissue injuries.

An adjuvant as used in the formulation may be a structural modulator. A "structural modulator" as used herein generally refers to any agent that modulates the structure of the tropocollagen or the formulation.

A structural modulator as used in the formulation may comprise a tropocollagen stabilizer. A tropocollagen stabilizer includes any agent that slows or prevents denaturation of the triple helix structure of the tropocollagen (or other macromolecular structure of the microfibrils, fibrils and fibers) at increased temperatures. A preferred example of a tropocollagen stabilizer is glycerol. Tropocollagen stabilizers are known in the art and included herein by reference. Additional tropocollagen stabilizers can be identified by routine procedures. Agents that can slow or prevent denaturation of tropocollagen at increased temperatures include agents with a hydroxyl group that can be incorporated into the water-chain structure of the tropocollagen. Agents that can slow or prevent the denaturation of tropocollagen at increased temperatures include polyols, sugars, and osmolytes. As used herein, the term "polyol" is synonymous with "sugar alcohol," "polyhydric alcohol," and "polyalcohol" and generally refers to a hydrogenated form of carbohydrate, whose carbonyl group (aldehyde or ketone, reducing sugar) has been reduced to a primary or secondary hydroxyl group (hence the alcohol), such as, e.g., mannitol from mannose, xylitol from xylose, and lactitol from lactulose. Non-limiting examples of polyols that can be used in the present invention include glycerol, threitol, arabitol, erythritol, ribitol, xylitol, galactitol (or dulcitol), gluctiol (or sorbitol), iditol, inositol, mannitol, isomaltitol, lactitol, maltitol, and polyglycitol.

Other non-limiting examples of polyols that can be used in the present invention can be found in, e.g., Pharmaceutical Dosage Forms and Drug Delivery Systems (Howard C. Ansel et al., eds., Lippincott Williams & Wilkins Publishers, 7th ed. 1999); Remington: The Science and Practice of Pharmacy (Alfonso R. Gemiaro ed., Lippincott, Williams & Wilkins, 20th ed. 2000); Goodman & Gilman's The Pharmacological Basis of Therapeutics (Joel G. Hardman et al., eds., McGraw Hill Professional, 10th ed. 2001); and Handbook of Pharmaceutical Excipients (Raymond C. Rowe et al., Alpha Publications, 4th edition 2003), each of which is hereby incorporated by reference in its entirety. Examples of a sugar that can be used in the present invention include fructose, glucose, glyceraldehydes, lactose, arabinose, mannose, xylose, ribose, rhamnose, galactose, maltose, sucrose, trehalose, sorbose, sucralose, melezitose and raffinose. Examples of osmolytes that may be used in the formulation include, but are not limited to, sugars (e.g., sucrose, glucose, trehalose, fructose, xylose, mannitose, fucose), polyols (e.g., glycerol, mannitol, sorbitol, glycol, inositol), zwitterionic compounds (e.g., taurine), free amino acids with no net charge (e.g., glycine, proline, valine, leucine, alanine, glutamine), derivatives of amino acids (e.g., glycine betaine, alternatively referred to as betaine), and trimethylamino N-oxide (TMAO). Betaine, betaine derivatives, and TMAO are examples of zwitterionic tetra-substituted amine derivatives, which also may be used in the formulation.

A structural modulator may be a formulation modulator. A formulation modulator for use in the formulation may include any agent that modulates the viscosity, inter-collagen interactions, or other physiochemical properties of the formulation. A preferred structural modulator will not have an adverse effect on the therapeutic properties of the formulation and will not cause adverse reactions to the host in the amounts intended for application to the wound.

A formulation modulator as used in the formulation may comprise a solvophobic agent. A "solvophobic agent" as used herein generally refers to any agent that stabilizes the triple-helical structure of the tropocollagen and at the same time weakens inter-tropocollagen interactions and reduces aggregation of the tropocollagen. Preferably, a solvophobic agent for use in the invention is non-toxic and does not cause unacceptable side effects at the concentrations and amount used in the formulation. Preferably the solvophobic agent used in the invention does not inhibit angiogenesis at the wound site. An illustrative example of a solvophobic agent is glycerol. Non-limiting examples of other solvophobic agents that may be used in the invention include but are not limited to ethylene glycol, urea, sodium thiocyanate, or guanadinium hydrochloride. Other such solvophobic agents known in the art may also be used in the invention.

A formulation modulator for use in the invention may include hygroscopic agents. A "hygroscopic agent" as used herein generally refers to any agent that provides or increases the hygroscopic properties of the formulation, which is the ability to absorb water. A formulation may be selected which includes hygroscopic agents in order to provide the invention with hygroscopic properties. In some embodiments the formulation is capable of absorbing water and exudate from the wound. Non-limiting examples of hygroscopic agents include sugars, alcohols, and salts, including deliquescent salts such as calcium chloride, magnesium chloride, zinc chloride, potassium carbonate, potassium hydroxide, potassium phosphate, carnallite, ferric ammonium citrate, and sodium hydroxide A formulation modulator for use in the invention may include a solvent. A solvent for use in the formulation includes any liquid with the ability to dissolve any other liquid or solid. A solvent may be used in the present invention for example to modulate the viscosity of the formulation or to modulate intra-collagen interactions. Non-limiting examples of solvents include acetonitrile, ethyl acetate, acetone, benzene, toluene, dioxane, dimethylformamide, chloroform, methylene chloride, ethylene chloride, carbon tetrachloride, chlorobenzene, acetone, methanol, ethanol, isopropanol and butanol. A combination of solvents may also be used.

A formulation modulator for use in the invention may comprise a chemotactic agent. A chemotactic agent for use in the formulation includes any substance used to enhance the infiltration, attachment and or growth of cells on or into the applied formulation in vivo. These substances include, but are not limited to, bioactive agents such cellular growth factors (e.g., TGF-beta, FGF, etc.), substances that stimulate chondrogenesis (e.g., BMPs that stimulate cartilage formation such as BMP-2, BMP-12 and BMP-13), factors that stimulate migration of cells to the matrix, factors that stimulate matrix deposition, anti-inflammatories (e.g., non-steroidal anti-inflammatories), immunosuppressants (e.g., cyclosporins), as well as other proteins, such as elastic fibers, reticular fibers, glycoproteins or glycosaminoglycans, such as heparin sulfate, chondroitin-4-sulfate, chondroitin-6-sulfate, dermatan sulfate, keratin sulfate, etc. For example, growth factors such as TGF-beta, with ascorbate, have been found to trigger cell differentiation and cartilage formation by chondrocytes. The bioactive agent may also be a cell retention agent, such as laminin, fibronectin or the like to adhere cells to the matrix, or may be an active inhibitor of cellular migration such as macrophage migration inhibitory factor (MIF). One of ordinary skill in the art will readily recognize that such agents may either be in the form of polypeptides or in the form of nucleic acid molecules encoding such polypeptides, such that upon implantation such nucleic acid molecules are taken up by the migrating cells and expressed.

An adjuvant as used in the formulation may comprise an enhancer. An enhancer for use in the formulation may be any agent that improves, potentiates, or otherwise enhances the ability of the formulation to promote tissue repair and regeneration.

An enhancer may comprise a matrix metalloproteinase (MMP) inhibitor. An MMP inhibitor for use in the formulation may be any agent that reduces or inhibits that activity of MMP. MMP inhibitors are known in the art and included here by reference. Other MMP inhibitors can be identified by routine procedures.

Chronic wounds are often characterized by the presence of excess MMP. In a normal wound, MMP's are known to degrade collagen during the remodeling process of wound healing. In chronic wounds, elevated MMP levels are believed to inhibit angiogenesis in the wound by degrading growth factors and angiogenic mediators. As a result of inhibiting angiogenesis, excess MMP levels also elevate the necrotic burden of the wound by preventing the formation of new blood vessels to support newly formed tissue, breaking down viable tissue, and contributing to wound exudate.

The excess levels of MMP in a chronic wound can be ameliorated through the use of MMP inhibitors. The MMP inhibitor may be a tissue inhibitor of MMP (hereinafter, "TIMP"), recombinant TIMP, or a derivative thereof. In related, more specific embodiments, the TIMP is TIMP-1, TIMP-2, TIMP-3 and TIMP-4, respectively. TIMPs are a family of proteins that are natural, specific physiological inhibitors of MMPs and are synthesized by the same cells that produce MMPs. TIMP-1, TIMP-2, TIMP-2, and TIMP-4 are the four TIMP molecules that have been identified to date. A TIMP that is unknown at the time of the present invention but is described in the art in the future is incorporated here by reference.

An MMP inhibitor for use in the formulation may be a chelating agent. A chelating agent is any agent that forms a complex with or sequesters certain metal ions, inactivating the ions so that they cannot normally react with other elements or ions. Preferably a chelating agent for use in the invention is a zinc chelating agent. A zinc chelating agent is an agent able to form a complex with or sequester a zinc ion. Preferably, a zinc chelating agent of the invention is non-toxic and does not cause unacceptable side effects at the dosages being administered. An illustrative example of a zinc chelating agent is calcium ethylenediaminetetra-acetic acid (EDTA). Other non-limiting examples of zinc chelating agents include, but are not limited to, diethyldithiocarbamate (DEDTC), 3-mercapto-D valine, bis(diethylthiocarbamoyl) disulfide, N,N,N',N'-tetrakis (2-pyridylmethyl)-ethylenediamine, N-(6-methoxy-8-quinolyl)-p-toluenesulfonamide, 8-hydroxy quinoline, 8-hyroxy quinoline-5-sulphonic acid, diethyl dithiocarbamate, phenanthroline and its derivatives, dipicolinate, diphenylthiocarbazone, dithizone, cimetidine, dipicolinic acid, clioquinol, tromethamine, diclofenac, ibuprofen, naproxen, piroxicam, indomethacin, ketoprofen, nabumetone, apazone, sulindac, meloxicam, tiaprofenic acid, flurbiprofen, tolfenamic acid, phenylbutazone, benzydamide, aspirin, salicylic acid or pharmaceutically acceptable salts or derivatives of any one of the aforementioned.

An MMP inhibitor may also be an antimicrobial agent. An illustrative example of an antimicrobial agent that inhibits MMP is doxycycline. Other non-limiting examples of antimicrobial agents known to inhibit MMP include tetracyclines, minocycline, and derivatives of such antimicrobial agents. The MMP inhibitor may also be marimstat or cipemastat.

An enhancer used in the formulation may comprise an antimicrobial agent.

Antimicrobial agents include any agent that is reduces or inhibits the reproduction or proliferation of microorganisms in a wound or other site of tissue injury. Antimicrobial agents used in the invention may include agents that are able to inhibit the reproduction or proliferation of gram negative bacteria such as *Neisseria* (e.g. *N. meningitis, N. gonorrhoeae*), and *Acinetobacter* or rods, such as *Bacteroides* (e.g. *B. fragilis*), *Bordetella* (e.g. *B. pertussis, B. parapertussis*), *Brucella* (e.g. *B. melitentis, B. abortus Bang, B. suis*), *Campylobacter* (e.g. *C. jejuni, C. coli, C. fetus*), *Citrobacter, Enterobacter, Escherichia* (e.g. *E. coli*), *Haemophilus* (e.g. *H. influenzae, H. para-influenzae*), *Klebsiella* (e.g. *K. pneumoniae*), *Legionella* (e.g. *L. pneumophila*), *Pasteurella* (e.g. *P. yersinia, P. multocida*), *Proteus* (e.g. *P. mirabilis, P. vulgaris*), *Pseudomonas* (e.g. *P. aeruginosa, P. pseudomallei, P. mailer*), *Salmonella* (e.g. *S. enteritidis, S. infantitis S. Dublin S. typhi, S. paratyphi, S. schottmulleri, S. choleraesuis, S. typhimurium*, or any of the 2,500 other serotypes), *Serratia* (e.g. *S. marscences, S. liquifaciens*), *Shigella* (e.g. *S. sonnei, S. flexneri, S. dysenteriae, S. boydii*), *Vibrio* (e.g. *V. cholerae, V. el tor*), and *Yersinia* (e.g. *Y. enterocolitica, Y. pseudotuberculosis, Y. pestis*). Antimicrobial agents used in the invention may include agents that are able to inhibit the reproduction or proliferation of gram positive bacteria such as *Streptococcus* (e.g. *S. pneumoniae, S. viridans, S. faecalis, S. pyogenes*), *Staphylococcus* (e.g. *S. aureus, S. epidermidis, S. saprophyticus, S. albus*), and rods, such as *Actinomyces* (e.g. *A. israelii*), *Bacillus* (e.g. *B. cereus, B. subtilis*,

*B. anthracis*), *Clostridium* (e.g. *C. botulinum, C. tetani, C. perfringens, C. difficile*), *Corynebacterium* (e.g. *C. diphtheriae*), *Listeria*, and *Providencia*. Antimicrobial agents used in the invention may include agents that are able to inhibit the reproduction or proliferation of other bacteria not listed here but known in the art.

Antimicrobial agents used in the invention may include agents that have an antimicrobial action through inhibition of cell wall synthesis, such as (3-lactams and vancomycin, preferably penicillins, such as amdinocillin, ampicillin, amoxicillin, azlocillin, bacampicillin, benzathine pinicillin G, carbenicillin, cloxacillin, cyclacillin, dicloxacillin, methicillin, mezlocillin, nafcillin, oxacillin, penicillin G, penicillin V, piperacillin, and ticarcillin; cephalosporins, such as the first generation drugs cefadroxil, cefazolin, cephalexin, cephalothin, cephapirin, and cephradine, the second generation drugs cefaclor, cefamandole, cefonicid, ceforanide, cefoxitin, and cefuroxime, or the third generation cephalosporins cefoperazone, cefotaxime, cefotetan, ceftazidime, ceftizoxime, ceftriaxone, and moxalactam; carbapenems such as imipenem; or monobactams such as aztreonam.

Antimicrobial agents used in the invention may include agents that have an antimicrobial action through inhibition of protein synthesis, such as chloramphenicol; other tetracyclines preferably demeclocycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, and polymyxin B, and erythromycins and lincomycins; antimicrobials with action through inhibition of nucleic acid synthesis in particular sulfonamides such as sulfacytine, sulfadiazine, sulfisoxazole, sulfamethoxazole, sulfamethizole, and sulfapyridine; trimethoprim, quinolones, novobiocin, pyrimethamine, and rifampin.

Antimicrobial agents used in the invention may include agents that are able to inhibit the reproduction or proliferation of bacteria causing caries (e.g. *Streptococcus mutans, Lactobacillus* spp.), bacteria causing periodontal disease (e.g. *Actinobacillus actinomycetemcomitans, Porphyromonas gingivalis, Prevotella intermedia, Peptostreptococcus micros, Campylobacter* (*Fusobacteria*), *Staphylococci, B. forsythus*), bacteria causing alveolitis etc. (e.g. *Staphylococcus, Actinomyces* and *Bacillus*), and bacteria causing periapical lesions (e.g. *Spirochetes* and all above).

Examples of antimicrobial agents include alcohols. An illustrative example of an alcohol is glycol. Other non-limiting examples of antimicrobial agents for use in the formulation include ethylene glycol, xylitol, mannitol, or sorbital.

Other examples of antimicrobial agents include the classes, aminoglycosides, macrolides, and tetracyclines. An antimicrobial agent for use in the formulation may be selected from any of the common antibiotic classes such as penicillins, cephalosporins, polymixins, quinolones, or sulfonamides.

"Tetracyclines" as defined herein generally refers to tetracycline or any tetracycline derivative, as described above, possessing antibiotic activity when administered above the required serum level threshold, as is known in the art.

Tetracycline, as well as the 5-OH (oxytetracycline, e.g. Terramycin) and 7-C1 (chlorotetracycline, e.g. Aureomycin) derivatives, exist in nature, and are all well known antibiotics. Semisynthetic derivatives such as 7-dimethylaminotetracycline (minocycline) and 6a-deoxy-5-hydroxy-tetracycline (doxycycline) are also known tetracycline antibiotics. Natural tetracyclines may be modified without losing their antibiotic properties, although certain elements of the structure must be retained to do so. Preferred antibiotic tetracyclines include tetracycline, doxycycline, demeclocycline, minocycline, and lymecycline.

The antimicrobial agent for use in the invention may include topical antimicrobial agents, such as a noble metal containing therapeutics, topical antiseptics, including but not limited to povidone-iodine, betadine, sodium hypochlorite, acetic acid, cationic antiseptics such as hexadecyltrimethylammonium bromine, chlorhexidine, and alkyldimethyl benzyl ammonium chloride, hydrogen peroxide, therapeutic proteins, and topical or systemic antibiotics, including antibiotics from the classes of ansamycins, carbacephem, carbapenems, glycopeptides, monobactams, polypeptides, quinolones, sulfonamides, penicillins, cephalosporins, fluoroquinolones, tetracyclines, macrolides, aminoglycosides, and lincosamides and from the group including clindamycin, erythromycin, tetracycline, metronidazole, mupirocin, fluticasone, bacitracin zinc, neomycin sulfate, and polymyxin B sulfate.

The antimicrobial agent for use in the invention may be an antibiotic such as gentamicin, kanamycin, neomycin, netilmicin, streptomycin, tobramycin, paromomycin, geldanamycin, herbimycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceffibuten, ceftizoxime, ceftriaxone, cefdinir, cefepime, teicoplanin, vancomycin, azithromycin, clarithromycin, cirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, bacitracin, colistin, polymyxin B, ciprofloxacin, enoxacin, gatifloxacin, levofloxacin, lomeflxacin, moxifloxacin, norfloxacin, ofloxacin, trovafloxacin, mafenide, prontosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincomycin, ethambutol, fusfomycin, fusidic acid, furazolidone, isoniazid, linezoilid, metronidazole, mupirocin, nitrofurantoin, platensimycin, pyrazinamide, quinupristin, dalfopristin, rifampin, rifampicin, tinidazole, etc.

The antimicrobial agent for use in the formulation may be a topical antiseptic. Non-limiting examples of topical antiseptics include povidone-iodine, betadine, sodium hypochlorite, acetic acid, cationic antiseptic, and hydrogen peroxide.

The antimicrobial agent may be a peptide. The peptide for use in the formulation may be a glycopeptide. "Glycopeptide" generally refers to oligopeptide (e.g. heptapeptide) antibiotics, characterized by a multi-ring peptide core optionally substituted with saccharide groups, such as vancomycin. Non-limiting examples of glycopeptides included in this category of antimicrobials for use in the formulation may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591, 714; 5,840,684; and 5,843, 889; in EP 0 802 199; EP 0 801 075; EP 0 667 353; WO 97/28812; WO 97/38702; WO 98/52589; WO 98/52592;

and in J. Amer. Chem. Soc, 1996, 118, 13107-13108; J. Amer. Chem. Soc, 1997, 119, 1204112047; and J. Amer. Chem. Soc, 1994, 116, 4573-4590. Non-limiting representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chlooorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on Vancomycin by mild hydrolysis gives vancomycin aglycone. Also included within the scope of the term "glycopeptide antibiotics" are synthetic derivatives of the general class of glycopeptides disclosed above, including alkylated and acylated derivatives. Additionally, within the scope of this term are glycopeptides that have been further appended with additional saccharide residues, especially aminoglycosides, in a manner similar to vancosamine.

The term "lipidated glycopeptide" as used herein, generally refers specifically to those glycopeptide antibiotics which have been synthetically modified to contain a lipid substituent. As used herein, the term "lipid substituent" generally refers to any substituent that contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well-known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, and WO 00/39156.

The antimicrobial agent may be an antiviral including without limitation non-nucleoside reverse transcriptase inhibitors, nucleoside reverse transcriptase inhibitors, protease inhibitors, and nucleotide analog reverse transcriptase inhibitors.

An enhancer used in the formulation may comprise a cytokine. A cytokine for use in the formulation may include cell signaling proteins that promote re-epithelialization, angiogenesis, matrix production, and scar formation. An illustrative example of a cytokine is PDGF. Other non-limiting examples of cytokines include IL-la, IL-113, IL-2, IL-3, 1-4, IL-5, IL-6, IL-7, IL-8, IL-10, IL-12, IL-18, IL-21, IL-23, IFN-a, IFN-13, MIP-la, MIP-113, TGF-13, TNFa, and TNF-13. Examples of chemokines include BCA1/BLC, BRAK, Chemokine CC-2, CTACK, CXCL-16, ELC, ENA, ENA-70, ENA-74, ENA-78, Eotaxin, Exodus-2, Frac-30 talkine, GCP-2, GRO, GRO alpha (MGSA), GRO-beta, GRO-gamma, HCC-1, HCC-4, 1-309, IP-10, 1-TAC, LAG-1, LD78-beta, LEC/NCC-4, LL-37, Lymphotactin, MCP, MCAF (MCP-1), MCP-2, MCP-3, MCP-4, MDC, MDC, MDC-2, MDC-4, MEC/CCL28, MIG, MIP, MIP-1 alpha, MIP-1 beta, MIP-1 delta, MIP-3/MPIF-1, MIP-3 alpha, MIP-3 bet, MIP-4 (PARC), MIP-5, NAP-2, PARC, PF-4, RANTES, RANTES-2, SDF-1 alpha, SDF-1 beta, TARC, and TECK. The cytokine may be a growth factor. Examples of growth factors include Human Amphiregulin, Human Angiogenesis Proteins, Human ACE, HumanAngiogenin, HumanAngiopoietin, Human Angiostatin, Human Betacellulin, Human BMP, Human BMP-13/CDMP-2, Human BMP-14/CDMP-1, Human BMP-2, Human BMP-3, Human BMP-4, Human BMP-5, Human BMP-6, Human BMP-7, Human BMP-8, Human BMP-9, Human Colony Stimulating Factors, Human flt3-Ligand, Human GCSF, Human GM-CSF, Human M-CSF, Human Connective Tissue Growth Factor CTGF, Human Cripto-1, Human Cryptic, Human ECGF, Human EGF, Human EG-VEGF, Human Erythropoietin, Human Fetuin, Human FGF, Human FGF-1, Human FGF10, Human FGF-16, Human FGF-17, Human FGF-18, Human FGF-19, Human FGF2, Human FGF-20, Human FGF-3, Human FGF-4, Human FGF-5, Human FGF-6, Human FGF-7/KGF, Human FGF-8, Human FGF-9, Human FGF-acidic, Human FGF-basic, Human GDF-11, Human GDF-15, Human Growth Hormone Releasing Factor, Human HB-EGF, Human Heregulin, Human HGF, Human IGF, Human IGF-I, Human IGF-II, Human Inhibin, Human KGF, Human LCGF, Human LIF, Human Miscellaneous Growth Factors, Human MSP, Human Myo-60 statin, Human Myostatin Propeptide, Human Nerve Growth Factor, Human Oncostatin M, Human PD-ECGF, Human PDGF, Human PDGF (AA Homodimer), Human PDGF (AB Heterodimer), Human PDGF (BB Homodimer), Human PDGF (CC Homodimer), Human PIGF, Human PIGF, Human PIGF-1, Human PIGF-2, Human SCF, Human SMDF, Human Stem Cell Growth Factor, Human SCGF alpha, Human SCGF-beta, Human Thrombopoietin, Human Transforming Growth Factor, Human TGF-alpha, Human TGF-beta, and Human VEGF. Any cytokine not listed here but described in the art and any cytokine unknown at the time of the present invention but described in the art in the future is incorporated here by reference.

An enhancer used in the formulation may include a wound healing agent. A wound healing agent for use in the invention includes any agent that has the capacity to promote wound healing, tissue repair and/or tissue regeneration. Wound healing agents include, without limitation, dermatologically active agents including agents for treating wound healing, inflammation, acne, psoriasis, cutaneous aging, skin cancer, impetigo, herpes, chickenpox, dermatitis, pain, itching, and skin irritation. Non limiting examples of such dermatologically active agents include hydrocortisone, dexamethesone, panthenol, phenol, tetracycline hydrochloride, yeast, hexylresorcinol, lamin, kinetin, betamethasone, triamcinolone, fluocinolone, methylprednisolone, dapsone, sulfasalazine, resorcinol, salicylic acid, benzoyl peroxide, erythromycin-benzoyl peroxide, erythromycin, clindamycin, mupirocin, griseofulvin, azoles such as miconazole, econozole, itraconazole, fluconazole, andketoconazole, ciclopirox, allylamines such as naftifine and terfinafine, acyclovir, famciclovir, valacyclovir, benzocaine, lidocaine, dibucaine, pramoxine hydrochloride, methyl salicylate, camphor, menthol, resocinol, and vitamins such as tocopherol, and tocopherol acetate.

Wound healing agents for use in the formulation may include agents that promote the endogenous production of nitric oxide by endothelial cells. Wound healing agents for use in the present invention may also include any bioactive agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Non-limiting examples of such wound-healing agents are aminoxyls, furoxans, nitrosothiols, nitrates and anthocyanins; nucleosides, such as adenosine; and nucleotides, such as adenosine diphosphate (ADP) and adenosine triphosphate (ATP); neurotransmitter/neuromodulators, such as acetylcholine and 5-hydroxytryptamine (serotonin/ 5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP), and proteins, such as insulin, vascular endothelial growth factor (VEGF), and thrombin. Such wound healing agents may also include any compound (e.g., polymer) bound to a nitric oxide releasing functional group. Non-limiting examples of compounds bound to a nitric oxide releasing functional group are S-nitrosothiol derivative (adduct) of bovine or human serum albumin and as disclosed, e.g., in U.S. Pat. No. 5,650,447.

Wound healing agents for use in the formulation may include monoclonal antibodies directed against known surface markers of progenitor endothelial cells (PECs). Circulating endothelial progenitor cells are some way along the developmental pathway from (bone marrow) monocytes to mature endothelial cells. Small proteinaceous motifs, such as the B domain of bacterial Protein A and the functionally equivalent region of Protein G, that are known to bind to, and thereby capture, such antibody molecules can be covalently attached to polymers and act as ligands to capture antibodies by the Fc region out of the host's blood stream. Therefore, the antibody types that can be attached to polymers using a Protein A or Protein G functional region are those that contain an Fc region. The captured antibodies will in turn bind to and hold captured progenitor endothelial cells near the polymer surface while other activating factors, such as the bradykinins, activate the progenitor endothelial cells.

Complementary determinants (CDs) that have been reported to decorate the surface of endothelial cells include CD31, CD34+, CD34−, CD102, CD105, CD106, CD109, CDwl30, CD141, CD142, CD143, CD144, CDwl45, CD146, CD147, and CD166. These cell surface markers can be of varying specificity and the degree of specificity for a particular cell/developmental type/stage is in many cases not fully characterized. In addition these cell marker molecules against which antibodies have been raised will overlap (in terms of antibody recognition) especially with CDs on cells of the same lineage: monocytes in the case of endothelial cells. CDs 106, 142 and 144 have been reported to mark mature endothelial cells with some specificity. CD34 is presently known to be specific for progenitor endothelial cells and therefore is currently preferred for capturing progenitor endothelial cells out of circulating blood in the site into which the formulation is implanted. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies, as are known in the art.

Wound healing agents for use in the present invention may include wound healing cells. Non-limiting examples of wound healing cells that can be used in the formulation include, for example, pericytes and endothelial cells, including progenitor endothelial cells.

An additional category of wound healing cells that may be used in the formulation are inflammatory healing cells. Wound healing cells may be implanted directly into the formulation or recruited to the wound site by means of ligands for such cells, such as antibodies and smaller molecule ligands, whether biologics or synthetic, that specifically bind to various "cellular adhesion molecules" (CAMs). Non-limiting examples of such ligands are ICAM-1 (CD54 antigen); ICAM-2 (CD102 antigen); ICAM-3 (CD50 antigen); ICAM-4 (CD242 antigen); and ICAM-5; Vascular cell adhesion molecules (VCAMs), such as VCAM-1 (CD106 antigen); Neural cell adhesion molecules (NCAMs), such as NCAM-1 (CD56 antigen); or NCAM-2; Platelet endothelial cell adhesion molecules PECAMs, such as PEC AM-1 (CD31 antigen); Leukocyte endothelial cell adhesion molecules (ELAMs), such as LECAM-1; or LECAM-2 (CD62E antigen), and the like.

In another aspect, the wound healing agents include extra cellular matrix proteins, which are macromolecules that can be dispersed in the formulation. Examples of useful extra-cellular matrix proteins for this purpose include, for example, glycosaminoglycans, usually linked to proteins (proteoglycans), and fibrous proteins (e.g., collagen; elastin; fibronectins and laminin). Biomimics of extra-cellular proteins can also be used. These are usually non-human but biocompatible glycoproteins, such as derivatives of alginates and chitin. Wound healing peptides that are specific fragments of such extra-cellular matrix proteins or their bio-mimics can also be used.

Wound healing agents for use in the formulation include drugs that enable healing. Such healing enabler drugs include, for example, anti-inflammatory agents as well as certain healing promoters, such as, for example, vitamin A and synthetic inhibitors of lipid peroxidation.

Wound healing agents for use in the formulation may include anti-inflammatory agents. Anti-inflammatory agents include any agent that reduces inflammation. Non-limiting examples of anti-inflammatory agents include analgesics (e.g., NSAIDS and salicyclates), antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, Physician's Desk Reference, 2005 Edition, incorporated herein by reference. An illustrative example of an anti-inflammatory agent is dexamethasone. Alternatively, the anti-inflammatory agent can include sirolimus (rapamycin), which is a triene macrolide antibiotic isolated from Steptomyces hygroscopicus.

A wound healing agent for use in the invention may also comprise a pharmaceutical composition for promoting neovascularization and angiogenesis. A pharmaceutical composition for promoting neovascularization and angiogenesis may comprise a steroid. Steroids suitable for use in the invention will preferably not have any toxic or negative side effects at the dosage used in the formulation. Non-limiting examples of steroids include angiostatic steroids such as tetrahydro-steroids, including tetrahydrocortisol (THF), tetrahydrocortisone (THE) and tetrahydrocortexolone (THS).

A wound healing agent for use in the invention may comprise a pharmaceutical composition that promotes the expression of procollagen. A pharmaceutical composition that promotes the expression of procollagen may include an anabolic steroid. Preferred anabolic steroids for use in the invention will increase collagen density, increase tensile strength, and increase cellularity of scar tissue. An illustrative example is of an anabolic steroid for use in the formulation is Oxandrolone. Methods of formulating compositions for administration are well know in the art, particularly the arts of pharmaceuticals and clinical medicine. See, e.g., Remington, The Science and Practice of Pharmacy, Alfonso R. Gennaro (Ed.) Lippincott, Williams & Wilkins (pub).

A wound healing agent for use in the invention may also comprise a glucocorticoid receptor antagonist.

It is known in the art that glucocorticoids increase the risk of wound infection and delay the healing of open wounds and inhibit or reduce endogenous collagen production. The effects of glucocorticoids can be reversed by a glucocorticoid receptor antagonists.

A glucocorticoid antagonist for use in the invention may include a steroidal anti-glucocorticoid. Various steroidal antiglucocorticoids can be obtained by modification of the basic structure of a known glucocorticoid such as Cortisol, i.e., varied forms of the steroid backbone. The structure of Cortisol, for example, can be modified in a variety of ways. The two most commonly known classes of structural modifications of the Cortisol steroid backbone to create glucocorticoid antagonists include modifications of the hydroxy group and modification of the side chain (see, e.g., Lefebvre, J. Steroid Biochem. 33:557-563, 1989).

Non-limiting examples of steroidal glucocorticoid receptor antagonists that may be used in the formulation include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127 and 6,303,591. Such steroidal glucocorticoid receptor antagonists for use in the formulation may include cortexolone, dexamethasone-oxetanone, 19-nordeoxycorticosterone, 19-norprogesterone, cortisol-21-mesylate; dexamethasone-21 mesylate, II(3-(4-dimethylaminoethoxyphenyl)-17apropynyl-17(3-hydroxy-4,9 estradien-3-one (RU009), and 17(3-hydroxy-17a-19-(4-methylphenyl)androsta-4,9(II) dien-3-one (RU044).

Other non-limiting examples of steroidal antiglucocorticoids are disclosed in Van Kampen et al. (2002) Eur. J. Pharmacol. 457(2-3):207, WO 03/043640, EP 0 683 172 BI, and EP 0 763 541 BI, each of which is incorporated herein by reference.

A wound healing agent for use in the formulation may comprise a glucocorticoid agonist with a modified steroidal backbone comprising a substitution of the II-(3 hydroxy group. This class includes natural antiglucocorticoids, including cortexolone, progesterone and testosterone derivatives, and synthetic compositions, such as mifepristone (Lefebvre, et al. supra). Embodiments of the invention include steroid backbone derivatives because these compounds are devoid of progesterone receptor (PR) binding activity (Agarwal, FEBS 217:221-226, 1987). Another embodiment comprises an II-(3 phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a II-(3 phenyl-aminodimethyl steroid, the steroid receptor is maintained in a conformation that cannot bind its natural ligand, such as Cortisol in the case of glucocorticoid receptor (Cadepond, 1997, supra).

Synthetic II-(3 phenyl-aminodimethyl steroids include mifepristone, also known as RU486, or 17-(3-hydrox-II-(3-(4-dimethyl-aminophenyl)17-a-(I-propynyl)estra-4,9-dien-3-one). Mifepristone has been shown to be a powerful antagonist of both the progesterone and glucocorticoid (glucocorticoid receptor) receptors. Another II-(3 phenyl-aminodimethyl steroids shown to have glucocorticoid receptor antagonist effects includes RU009 (RU39.009), II-|3-(4-dimethyl-aminoethoxyphenyl)-17-a(propynyl-17 (3-hydroxy-4,9-estradien-3-one) (see Bocquel, J. Steroid Biochem. Molec. Biol. 45:205-215, 1993). Another glucocorticoid receptor antagonist related to RU486 is RU044 (RU43.044) 17-|3-hydrox-17-a-19-(4-methyl-phenyl)androsta-4,9 (II)-dien-3-one) (Bocquel, 1993, supra). See also Teutsch, Steroids 38:651-665, 1981; U.S. Pat. Nos. 4,386,085 and 4,912,097.

One embodiment includes compositions containing the basic glucocorticoid steroid structure which are irreversible anti-glucocorticoids. Such compounds include a-keto-methanesulfonate derivatives of Cortisol, including cortisol-21-mesylate (4-pregnene-II-(3,17-a, 21-triol-3,20-dione-21-methane-sulfonate and dexamethasone-21-mesylate (16-methyl-9 a-fhioro-I,4-pregnadiene-II|3, 17-a, 21-triol-3, 20-dione-21-methane-sulfonate). See Simons, J. Steroid Biochem. 24:25-32, 1986; Mercier, J. Steroid Biochem. 25:11-20, 1986; U.S. Pat. No. 4,296,206.

Steroidal antiglucocorticoids which can be obtained by various structural modifications of the 17-(3 side chain are also used in the methods of the invention. This class includes synthetic antiglucocorticoids such as dexamethasone-oxetanone, various 17, 21-acetonide derivatives and 17-|3-carboxamide derivatives of dexamethasone (Lefebvre, 1989, supra; Rousseau, Nature 279:158-160, 1979).

Glucocorticoid receptor antagonists used in the various embodiments of the invention include any steroid backbone modification which effects a biological response resulting from a glucocorticoid receptor-agonist interaction. Steroid backbone antagonists can be any natural or synthetic variation of Cortisol, such as adrenal steroids missing the C-19 methyl group, such as 19-nordeoxycorticosterone and 19-norprogesterone (Wynne, Endocrinology 107:12781280, 1980).

In general, the II-(3 side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, Mol. Pharm. 52:749-753, 1997), Org31710 (see Mizutani, J Steroid Biochem Mol Biol 42(7):695-704, 1992), RU43044, RU40555 (see Kim, J Steroid Biochem Mol Biol. 67(3): 21322, 1998), RU28362, and ZK98299.

Non-limiting examples of non-steroidal glucocorticoid receptor antagonists include clotrimazole; N (triphenylmethyl)imidazole; N-([2-fluoro-9-phenyl]fluorenyl)imidazole; N-([2-pyridyl]diphenylmethyl)imidazole; N (2 [4,4', 4"-trichlorotrityl]oxyefhyl)morpholine; I-(2 [4,4',4"-trichlorotrityl]oxyethyl)-4 (2 hydroxyethyl)piperazine dimaleate; N-([4,4',4"]-trichlorotrityl)imidazole; 9-(3-mercapto-I,2,4 triazolyl)9-phenyl-2,7-difluorofluorenone; I-(2-chlorotrityl)-3,5dimethylpyrazole; 4 (morpholinomefhyl)-A-(2pyridyl)benzhydrol; 5-(5-methoxy-2-(N-methylcarbamoyl)phenyl)dibenzosuberol; N-(2-chlorotrityl)-L-prolinol acetate; I-(2-chlorotrityl)-2-methylimidazole; 1 (2 chlorotrityl)-I,2,4-triazole; I,S-bis(4, 4',4"-trichlorotrityl)-I,2,4triazole-3-thiol; and N((2,6 dichloro-3 methylphenyl)diphenyl)methylimidazole (see U.S. Pat. No. 6,051,573); the glucocorticoid receptor antagonist compounds disclosed in U.S. Pat. Nos. 5,696,127 and 6,570,020; the GR antagonist compounds disclosed in US Patent Application 20020077356, the glucocorticoid receptor antagonists disclosed in Bradley et al, J. Med.

Chem. 45, 2417-2424 (2002), e.g., 4a(S)-Benzyl-2(R)-chloroethynyl-1,2,3,4,4a, 9,10,10a(R)-octahydro-phenanthrene-2,7-diol ("CP 394531") and 4a(S)-Benzyl-2(R)-prop-I-ynyl-1,2,3,4,4a,9, 10,10a(R)-octahydro-phenanthrene-2,7-diol ("CP 409069"); the compound (II|3,17|3)-II-(1,3-benzodioxol-5yl)-17-hydroxy-17-(I-propynyl)estra-4,9-dien-3-one ("ORG 34517") disclosed in Hoyberg et al, Int'l J. of Neuro-psychopharmacology, 5:Supp. 1, S148 (2002); the compounds disclosed in PCT International Application No. WO 96/19458, which describes non-steroidal compounds which are high-affinity, highly selective antagonists for steroid receptors, such as 6-substituted-I,2-dihydro-N protected-quinolines; and some K opioid ligands, such as the K opioid compounds dynorphin-1,13 diamide, U50,488 (trans (IR,2R)-3,4-dichloro-N-methyl-N-[2-(I-pyrrolidinyl)cyclohexylbenzeneacetamide), bremazocine and ethylketocyclazocine; and the non-specific opioid receptor ligand, naloxone, as disclosed in Evans et al., Endocrin., 141:2294 2300 (2000).

A non-steroidal glucocorticoid receptor antagonist for use in the formulation may also be an antibody directed at the glucocorticoid receptor.

An enhancer for use in the invention may include a therapeutic protein. A therapeutic protein for use in the invention may include any peptide, polypeptide, or protein that has the capacity to promote wound healing, tissue repair, or tissue regeneration. Therapeutic proteins include enzymes, blood factors, blood clotting factors, insulin, erythropoietin, interferons, including interferon-a, interferon-(3, protein C, hirudin, granulocyte-macrophage colony-stimulating factor, somatropin, epidermal growth factor, albumin, hemoglobin, lactoferrin, angiotensin-converting enzyme, glucocerebrosidase, human growth hormone, VEGF, antibodies, and monoclonal antibodies.

Specific growth factors include but are not limited to growth factors selected from families such as transforming growth factor-beta (TGF-(3), bone morphogenic protein (BMP), neurotrophins (NGF, BDNF, and NT3), a fibroblast growth factor (FGF), for example, acidic fibroblast growth factor (aFGF or FGF-1) and basic fibroblast growth factor (bFGF or FGF-2), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF9), epidermal growth factor (EGF), and hepatocyte growth factor (HGF).

An enhancer for use in the present invention may comprise a nucleic acid or transgene for delivery to cells of the host. Such an enhancer may further comprise a viral vector.

Nucleic acids delivered to the cell by the virus according to the invention may be stably integrated into the genome of the cell or may be maintained in the cell as separate episomal segments of nucleic acid. While integrating virus vectors may be used, non-integrating systems, which do not transmit the virus genome or transgene to daughter cells for many generations are preferred for wound healing. In this way, the transgene product is expressed during the wound healing process, and as the transgene is diluted out in progeny generations, the amount of expressed transgene product is diminished.

In certain embodiments of the invention, adenovirus or adenovirus-derived viruses are utilized for introduction of one or more transgenes. Examples of virus vectors utilized by the invention include intact adenovirus, replication-defective adenovirus vectors requiring a helper plasmid or virus in production of the virus particles, and adenovirus vectors with their native tropism modified or ablated including adenoviral vectors containing a targeting ligand. In specific embodiments, the targeting ligand is a polypeptide reactive with a cell surface receptor such as an FGF receptor. Vector compositions, systems and methods for using these adenovirus vectors are disclosed in WO 98/40508 that is incorporated by reference in its entirety. Other references describing adenovirus vectors and other virus vectors which could be used in the compositions and methods of the present invention include the following: Horwitz, pp. 1679-1721, Adenoviridae and Their Replication, in Fields et al. (eds.) Virology, Vol. 2 (1990) Raven Press New York; Graham et al., pp. 109-128 in Methods in Molecular Biology, Vol. 7: Gene Transfer and Expression Protocols, Murray, E. (ed.), Humana Press, Clifton, N.J. (1991); Miller et al. (1995) FASEB J. 9:190-199; Schreier (1994) Pharmaceutica Acta Helvetiae 68:145-159; Curiel et al. (1992) Hum. Gene Ther. 3:147-154; WO 95/00655; WO 95/16772; WO 95/23867; WO 94/26914; WO 95/02697; WO 95/25071). A variety of adenovirus-based plasmids are also available from commercial sources, including, e.g., Microbix Biosystems of Toronto, Ontario (see, e.g., Microbix Product Information Sheet: Plasmids for Adenovirus Vector Construction, 1996).

Various adeno-associated virus (AAV) vector systems have also been developed for polynucleotide delivery. By way of illustration, AAV vectors useful in the methods and compositions of the present invention are preferably replication-deficient in humans, for example, due to deletion of the rep and/or cap genes, essential to AAV replication, and the transgene (including associated promoters and other regulatory sequences) inserted therein is preferably flanked by AAV inverted terminal repeat (ITR) sequences. The resulting recombinant AAV vector is then replicated in a packaging cell line supplying the missing AAV functions (i.e., the rep and/or cap genes) in trans. AAV vectors can be readily constructed using techniques well known in the art. See, e.g., U.S. Pat. Nos. 5,173,414 and 5,139,941; WO 92/01070; WO 93/03769; WO 96/17947; WO 99/11764; Lebkowski et al. (1988) Molec. Cell. Biol. 8:3988-3996; Samulski et al. (1989) J. Virol. 63:3822-3828; Vincent et al. (1990) Vaccines 90 (Cold Spring Harbor Laboratory Press); Berns, Virology, pp. 1743-1764 (Raven Press 1990); Carter (1992) Curr. Opin. Biotechnol. 3:533-539; Muzyczka (1992) Curr. Top. Microbiol. and Immunol. 158:97-129; Kotin (1994) Hum. Gene Ther. 5:793-801; Shelling and Smith (1994) Gene Therapy 1:165-169; and Zhou et al. (1994) J. Exp. Med. 179:1867-1875; Chatterjee et al. (1995) Ann. NY Acad. Sci. 770:79-90; Flotte et al. (1995) Gene Therapy 2:357-362; Du et al. (1996) Gene Therapy 3:254-261; Kaplitt et al. (1996) Ann. Thorac. Surg. 62:1669-1676; Zolotukhin et al. (1999) Gene Therapy 6:973-985.

In other embodiments, the present invention can employ recombinant retroviruses for the introduction of the transgene. Methods of producing recombinant retroviral virions suitable for gene therapy have been extensively described (see, e.g., Mann et al. (1983) Cell 33:153; Nikolas and Rubenstein, Vectors: A survey of molecular cloning vectors and their uses, Rodriquez and Denhardt (eds.), Stoneham: Butterworth, 494-513, 1988). By way of illustration, the lentivirus genus of retroviruses (for example, human immunodeficiency virus (HIV), feline immunodeficiency virus (FIV) and the like) can be modified so that they are able to transduce cells that are typically non-dividing (see, e.g., Naldini et al. (1996) Science 272:263-267; Miyoshi et al. (1998) J. Virol. 72:8150-8157; and Buchschacher et al. (2000) Blood 15:2499-2504; U.S. Pat. No. 6,013,516).

While HIV-based lentiviral vector systems have received some degree of focus in this regard, other lentiviral systems have recently been developed, such as FIV-based lentivirus vector systems, that offer potential advantages over the HIV-based systems (see e.g., Poeschla et al. (1998) Nat. Med. 4:354-357; Romano et al. (2000) Stem Cells 18:19-39 and references reviewed therein).

Packaging cell lines suitable for use with the above-described virus vector constructs may be readily prepared and used to create producer cell lines (also termed virus vector cell lines) for the production of recombinant virus particles.

The present compositions and methods may employ a variety of transgenes encoding different types of therapeutic agents. The transgenes may code for a variety of therapeutic agents that promote tissue repair, angiogenesis or regeneration, including extracellular, cell surface, and intracellular proteins and RNAs. Examples of extracellular proteins include growth factors, cytokines, extracellular matrix molecules, therapeutic proteins, hormones and peptide fragments of hormones, inhibitors of cytokines, peptide growth and differentiation factors, interleukins, chemokines, interferons, colony stimulating factors and angiogenic factors. Examples of proteins include tissue metalloproteinase inhibitors including TIMP-1, TIMP-2, TIMP-3 and TIMP-4. Examples of such proteins include, but are not limited to, the superfamily of TGF-beta molecules, including the TGF-beta isoforms and bone morphogenetic proteins (BMPs) such as BMP2, BMP3, BMP4, BMP5, BMP6, BMP7, BMP8, BMP9, BMP10, BMP11, BMP12, or BMP13; cartilage-derived morphogenic protein (CDMP); latent TGF-beta binding proteins (LTBPs); keratinocyte growth factor (KGF); hepatocyte growth factor (HGF); platelet derived growth factor (PDGF); insulin-like growth factor (IGF); the fibroblast growth factors (FGF-1, FGF-2, etc.), epidermal growth factors (EGFs); connective tissue growth factor (CTGF); skeletal growth factor (SGF); vascular endothelial growth factor (VEGF); leukemia inhibitory factor (LIF); parathyroid hormone-related peptide (PTHrP); activins; inhibins; interleukins (IL); macrophage-colony stimulating factor (M-CSF); and granulocyte macrophage-colony stimulating factor (GM-CSF). In specific embodiments, the polypeptide growth factor is, for example, PDGF-AA, PDGF-BB, PDGF-AB, HGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, TGF-alpha, TGF-beta1, TGF-beta2, or TGF-beta3.

In a further embodiment, the transgene may encode for a zinc-finger binding protein, cell survival factors (e.g. BCL-2), transcription factors, or mono or polyclonal antibodies or soluble receptors that bind to mediators of inflammation. Hormones that may be used in the practice of the invention include, for example, growth hormone (GH) and parathyroid hormone (PTH). Examples of extracellular proteins also include the extracellular matrix proteins (or fragments thereof) such as collagen, laminin, and fibronectin. Examples of cell surface proteins include the family of cell adhesion molecules (e.g., the integrins, selectins, Ig family members such as N-CAM and L1, and cadherins); cytokine signaling receptors such as the TGF receptors and the FGF receptor; and non-signaling co-receptors such as betaglycan and syndecan. Examples of intracellular RNAs and proteins include the family of signal transducing kinases, cytoskeletal proteins such as talin and vinculin, cytokine binding proteins such as the family of latent TGF-beta binding proteins, and nuclear trans-acting proteins such as transcription factors, chromatin-associated proteins, and proteins which regulate mRNA stability and turnover.

The transgenes may also code for proteins that block pathological processes, thereby allowing the natural wound healing process to occur unimpeded. Examples of blocking factors include ribozymes that destroy RNA function and transgenes that, for example, code for tissue inhibitors of enzymes that destroy tissue integrity, e.g., inhibitors of metalloproteinases associated with arthritis.

One may obtain the transgene encoding the protein or therapeutic agent of interest using a variety of molecular biological techniques, generally known to those skilled in the art. For example, cDNA or genomic libraries may be screened using primers or probes with sequences based on the known nucleotide sequences. Polymerase chain reaction (PCR) may also be used to generate the transgene fragment encoding the therapeutic agent of interest. Alternatively, the transgene may be obtained from a commercial source. Nucleic acid sequences of interest are available in the art and from Genbank databases.

The transgenes useful in the present invention include those possessing naturally occurring nucleotide sequences and functional variants thereof. Polypeptides can be encoded by transgene nucleic acids that, by virtue of the degeneracy of the genetic code, are not identical in sequence to naturally occurring genes, cDNAs, or mRNAs. Variants and mutants can include amino acid substitutions, additions or deletions. Amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues. Conservative amino acid substitutions are those that preserve the general characteristics of the polypeptide, including charge, hydrophobicity/hydrophilicity, and/or steric bulk of the amino acid substituted.

Techniques for introducing changes in nucleotide sequences that are designed to alter the functional properties of the encoded proteins or polypeptides are well known in the art. Such modifications include the deletion, insertion or substitution of bases that result in changes in the amino acid sequence. Changes may be made to increase the activity of an encoded protein, to increase its biological stability or half-life, to change its glycosylation pattern, confer temperature sensitivity or to alter the expression pattern of the protein and the like. All such modifications to the nucleotide sequences are encompassed by this invention.

The transgene encoding the translational or transcriptional products of interest may be recombinantly engineered to contain the necessary elements for directing the transcription and/or translation of the transgene sequence by the repair cells at the wound in vivo following virus infection or uptake. Methods which are well known to those skilled in the art can be used to construct expression vectors containing the protein coding sequence operatively associated with appropriate transcriptional/translational control signals. These methods include in vitro recombinant DNA techniques, and synthetic techniques. See, for example, the techniques described in Sambrook, et al., 1992, Molecular Cloning, A Laboratory Manual, Cold Spring Harbor Laboratory, N.Y. and Ausubel et al., 1989, Current Protocols in Molecular Biology, Greene Publishing Associates & Wiley Interscience, N.Y.

The transgenes encoding the therapeutic agents of interest may be operatively associated with a variety of different promoter/enhancer elements. The expression elements of these vectors may vary in their strength and specificities.

The promoter may be in the form of the promoter which is naturally associated with the gene of interest, an endogenous promoter. Alternatively, the transgene may be positioned under the control of a recombinant or heterologous promoter, i.e., a promoter that is not normally associated with that gene. The promoter may be either constitutive or regulated. For example, tissue specific promoter/enhancer elements may be used to regulate the expression of the transferred DNA in specific cell types. Examples of transcriptional control regions that exhibit tissue specificity which have been described and could be used include, but are not limited to: elastase I gene control region (Swift et al. (1984) Cell 38:639-646; Ornitz et al., Cold Spring Harbor Symp. Quant. Biol. (1986) 50:399-409; MacDonald (1987) Hepatology 7:42S-51S); insulin gene control region (Hanahan, Nature 315:115-122, 1985); immunoglobulin gene control region (Grosschedl et al., Cell 38:647-658, 1984; Adams et al., Nature 318:533-538, 1985; Alexander et al., Mol. Cell. Biol. 7:1436-1444, 1987): albumin gene control region (Pinkert et al., Genes and Devel. 1:268-276, 1987) alpha-fetoprotein gene control region (Krumlauf et al., Mol. Cell. Biol. 5:1639-1648, 1985; Hammer et al., Science 235:53-58, 1987); alpha-1-antitrypsin gene control (Kelsey et al., Genes and Devel. 1:161-171, 1987); beta-globin gene control region (Magram et al., Nature 315:338-340, 1985; Kollias et al., Cell 46:89-94, 1986); myelin basic protein gene control region (Readhead et al., Cell 48:703-712, 1987); myosin light chain-2 gene control region (Shani, Nature 314:283-286, 1985); and gonadotropic releasing hormone gene control region (Mason et al., Science 234:1372-1378, 1986). Promoters isolated from the genome of viruses that grow in mammalian cells, (e.g., RSV, vaccinia virus 7.5K, SV40, HSV, adenoviruses MLP, human elongation factor-1 alpha/HTLV (Hef-1 alpha/HTLV), MMTV LTR and CMV promoters) may be used, as well as promoters produced by recombinant DNA or synthetic techniques. It is understood that cells comprising the target tissue may be infected by the virus and express the therapeutic transgene. It may, therefore, be advantageous to use transgenes containing target tissue specific promoter/enhancer elements, and it is within the scope of the current invention to utilize such elements according to claimed methods and within claimed compositions. Thus, in certain embodiments, transgenes (and/or the virus containing the transgene) will be constructed to maximize expression in infiltrating repair cells, so as to provide a universal transgene for use in targeting a wide range of tissues. In other embodiments, transgenes (and/or the virus containing the transgene) may be constructed to maximize expression within target tissue cells. One preferred embodiment utilizes transgenes capable of high level expression in both infiltrating repair cells and target tissue cells.

In some instances, the promoter elements may be constitutive or inducible promoters and can be used under the appropriate conditions to direct high level or regulated expression of the transgene of interest. Expression of transgenes under the control of constitutive promoters does not require the presence of a specific substrate to induce gene expression and will occur under all conditions of cell growth. In contrast, expression of transgenes controlled by inducible promoters is responsive to the presence or absence of an inducing agent.

Specific initiation signals are also required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the protein coding sequences to ensure translation of the entire insert. These exogenous translational control signals and initiation codons can be of a variety of origins, both natural and synthetic. The efficiency and control of expression may be enhanced by the inclusion of transcription attenuation sequences, enhancer elements, etc.

It is within the scope of the invention that multiple transgenes combined on a single genetic construct under control of one or more promoters may be used. Thus, an almost endless combination of different transgenes and genetic constructs may be employed, subject to the nucleic acid capacity of the virus which contains the transgene(s). Certain gene combinations may be designed to, or their use may otherwise result in, achieving synergistic effects on cell stimulation and regeneration, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It is also within the scope of the invention that transgenes used in the invention include those encoding recombinant fusion proteins. Fusion proteins may consist of two or more polypeptides or fragments thereof. In certain embodiments, fusion proteins comprise a therapeutic polypeptide tagged with an immunogenic epitope such as the FLAG epitope (Kodak) which can be used to examine expression and delivery of the therapeutic protein by immunological methods known in the art such as ELISA, western blot or radioimmunoassay. In specific embodiments, fusion proteins contain a targeting moiety introduced to promote efficient uptake of a fused therapeutic polypeptide into target cells. Examples of targeting moieties include immunoglobulins and ligands which bind target cell surface receptors.

In addition to transgene sequences encoding therapeutic proteins, the scope of the present invention includes the use of transgenes encoding ribozymes or antisense RNA molecules that may be expressed in the mammalian repair cells. Such ribozymes and antisense molecules may be used to inhibit the translation of RNA encoding proteins of genes that inhibit a disease process or the wound healing process thereby allowing tissue repair to take place.

Antisense nucleic acids are designed to specifically bind to RNA, resulting in the formation of RNA-DNA or RNA-RNA hybrids and an arrest in DNA replication, reverse transcription or messenger RNA translation. Antisense nucleic acids based on a selected sequence can specifically interfere with expression of the corresponding gene. In the present invention, antisense nucleic acids are typically generated within the infected or transduced cell by expression from transgene constructs that contain the antisense strand as the transcribed strand. Antisense production and uses thereof are discussed extensively in the literature and are widely known and available to one skilled in the art.

Ribozymes are trans-cleaving catalytic RNA molecules possessing endoribonuclease activity. Ribozymes are specifically designed for a particular target nucleotide sequence. Ribozymes are engineered to cleave an RNA species site-specifically in the background of cellular RNA. The cleavage event renders the mRNA unstable and prevents protein expression. Preparation and usage of ribozymes is well known to the art (see, e.g., Usman et al. (1996) Current Opin. Struct. Biol. 6:527; Long et al. (1993) FASEB J. 7:25; Symons (1992) Ann. Rev. Biochem. 61:641; U.S. Pat. No. 5,254,678). Knowledge of the nucleotide sequence of the target ribonucleic acid molecule allows construction of an effective ribozyme.

An enhancer for use in the formulation may include conditioned medium. Conditioned medium generally refers to medium that has been incubated with cells and been used by the cells as a source essential amino acids, salts, vitamins, minerals, trace metals, sugars, lipids and nucleosides. Conditioned medium typically contains the nutrients of the original medium and cell products such as cytokines, proteins, extracellular matrix components, or any combination thereof, which have been synthesized and secreted by the cells into the medium. Conditioning is the process during which the cells synthesize and secrete of cytokines, proteins and extracellular matrix components, into the medium.

Preferably, the conditioned media of the invention are produced by cultured cells of skin cells; keratinocytes, dermal fibroblasts, or both, more preferably when the cells are cultured together as a co-culture of both keratinocytes and dermal fibroblasts. The conditioned media of the invention are most preferably produced when the co-culture is a cultured skin construct having at least a dermal layer and an epidermal layer arranged in orientation similar to native skin. Dermal layers comprise fibroblast cells, preferably of dermal origin and extracellular matrix, primarily of collagen. It will be appreciated by the skilled artisan that the cultured skin construct may contain, by either intentional addition or with continued culture of fibroblasts from primary sources, other cells found in skin and other extracellular matrix components.

Preferred cell types for use in this invention are derived from mesenchyme. More preferred cell types are fibroblasts, stromal cells, and other supporting connective tissue cells, or, as in the most preferred embodiment, human dermal fibroblasts. Human fibroblast cell strains can be derived from a number of sources, including, but not limited to neonate male foreskin, dermis, tendon, lung, umbilical cords, cartilage, urethra, corneal stroma, oral mucosa, and intestine. The human cells may include but need not be limited to: fibroblasts, smooth muscle cells, chondrocytes and other connective tissue cells of mesenchymal origin. It is preferred, but not required, that the origin of the matrix producing cell used in the production of a tissue construct be derived from a tissue type that it is to resemble or mimic after employing the culturing methods of the invention. For instance, a multilayer sheet construct is cultured with fibroblasts to form a living connective tissue construct; or myoblasts, for a skeletal muscle construct. More than one cell type can be used to fabricate a tissue construct. Cell donors may vary in development and age. Cells may be derived from donor tissues of embryos, neonates, or older individuals including adults. Embryonic progenitor cells such as mesenchymal stem cells may be used in the invention and induced to differentiate to develop into the desired tissue.

Although human cells are preferred for use in the invention, the cells to be used in the method of the are not limited to cells from human sources. Cells from other mammalian species including, but not limited to, equine, canine, porcine, bovine, feline, caprine, and ovine sources may be used. Murine cells, and other cells from rodent sources, may also be used. In addition, genetically engineered cells, recombinant cells, and cells that are spontaneously, chemically or virally transfected may also be used in this invention. For those embodiments that incorporate more than one cell type, mixtures of normal and genetically modified or transfected cells may be used and mixtures of cells of two or more species or tissue sources may be used, or both.

In one embodiment a wound healing agent for use in the formulation comprises stem cells. As used herein, the term "stem cell" generally refers to cells having developmental plasticity that are able to produce other cell types than the cells from which the stem cells are derived. To this end, they refer to as multipotent cells able to differentiate into a variety of cell types.

The stem cells of the present invention may be utilized to effectively populate the wounded area because of their multipotent or phenotypically broad differentiation potential, particularly the ability to differentiate into various wound healing cells and tissues and to replace, regenerate, or repair tissue. For example, stem cells may differentiate into types of tissue necessary to heal a wound, repair tissue, or regenerate tissue. Any type of stem cell or multipotent cell may be used in accordance with the present invention. Such stems cells may include any multipotent, pluripotent, or totipotent stem cells known in the art. For example, the stem cells may be human embryonic stem cells, murine embryonic stem cells, or other mammalian stem cells. Alternatively, stem cells may be isolated from human or murine umbilical cord blood or anyone other means associated with obtaining such cells. To this end, cells may be obtained from organisms, blastocysts, or cells isolated or created by suitable means known in the art. In other embodiments, the stem cells are multipotent adult stem cells and other stem cells that are able to give rise to myofibroblast-like cells when administered or cultured according to the methods described herein.

Regardless of origin, and as noted above, in one embodiment, a therapeutically effective amount of stem cells may be isolated and included in the formulation.

In a preferred embodiment the formulation comprises a physiologically acceptable excipient. A physiologically acceptable excipient for use in the invention may include any agent which is utilized in the formulation of a pharmaceutical agent as a pharmaceutical formulation, which is not deleterious to the animal to which the formulation may be administered, and which does not substantially affect the pharmaceutical activity of the pharmaceutical agent with which it is formulated. Typically, the physiologically acceptable excipients are employed for the purpose of facilitating formulation of the pharmaceutically active agent. Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient is preferably be stable under the conditions of manufacture and storage and is preferably be preserved against the contaminating action of microorganisms. Saline solutions and aqueous dextrose and glycerol solutions can also be employed as liquid excipients. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in Remington's Pharmaceutical Sciences pp. 1447-1676 (Alfonso R.

Gennaro, ed, 19th ed. 1995). Liquid carriers can be used in preparing solutions, suspensions, emulsions, syrups, and elixirs. A tropocollagen described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, scents, suspending agents, thickening agents, colors, viscosity regulators, stabilizers, or osmo-regulators. cellulose solution), alcohols (including monohydric alcohols and polyhydric alcohols, e.g., glycols) and their derivatives, and oils (e.g., fractionated coconut oil and arachis oil). The liquid carriers can be in sterile liquid form for administration.

A physiologically acceptable excipient may comprise a buffer in order to maintain a desirable pH of the matrix formula. A buffer for use in the invention may include a solution that has the property that its pH changes very little when a small amount of acid or base is added to it. In a preferred embodiment the formulation has a pH between 5 and 9. In a more preferred embodiment the formulation has a pH between 6 and 8. In a most preferred embodiment the formulation has a pH of about approximately 7.6.

The present invention relates to stable renatured tropocollagen formulations and methods of making and use thereof. These methods and formulations provide for a selectively flowable colloid suitable for storage for lengths of time and at temperatures that are amenable to pharmaceutical product processing, shipping, storage and use. In particular, the compositions of the present invention are stable when stored for substantial periods of time at temperatures well above the ultra-low temperatures (e.g., −70° C.). In a preferred embodiment, the composition is stable at standard refrigeration temperatures (e.g., 2° C. to 8° C.) for at least 18 months. In a more preferred embodiment, the composition is stable at standard refrigeration temperatures for at least two years. Preferably the composition is also stable at room temperatures (e.g., 20° C. to 25° C.) for at least 12 months.

In some embodiments the matrix and mammalian cell migration are associated through charge interactions. Accordingly, a formulation may be selected in order to provide appropriate charge interactions between the matrix and repair cells and also to provide a storage stable composition. In addition, the formulations are capable of supporting cellular ingrowth and harboring mammalian repair cells (e.g., via impregnation, adsorption, absorption, or chemical conjugation) so that repair cells are able to migrate into the matrix. One of ordinary skill in the art can readily determine whether a particular matrix is capable of cell ingrowth. At a minimum, the matrix must have chambers, pores, or openings large enough for a cell to enter. Such ingrowth can be analyzed by several methodologies, including seeding the matrix ex vivo and growing cells in culture on the matrix and subsequently analyzing the matrix for ingrowth. The matrix may then be removed and subjected to histological or microscopic analysis to determine the extent of cellular ingrowth. In particular embodiments ingrowth is initiated via a wound response. While the wound itself may be iatrogenic (e.g., caused directly or indirectly by a physician) or due to pathology or traumatic injury, its source is unimportant as long as wound response is ongoing or initiated at the site of matrix placement.

The formulation of the present invention comprises tropocollagen that is relatively homogenous throughout the formulation. Homogeneity requires that the tropocollagen has not aggregated. Preferably at least 75% of the tropocollagen has not aggregated. More preferably at least 90% of the tropocollagen has not aggregated. More preferably at least 95% of the tropocollagen has not aggregated.

Collagen used for the pharmaceutical preparation of the present invention may be obtained from a number of sources including the skin, bone, cartilage, tendons, or ligature of a mammal or fish. In a preferred embodiment the collagen is Type I collagen. In an exemplary embodiment the collagen is obtained from the skin of a bovine calf.

Various methods may be employed in preparing the formulation of the present invention. In a preferred embodiment the preparation includes the essential steps in which the collagen is solubilized in a dilute acid and then sterile filtered to select a homogenous content of renatured tropocollagen. In a preferred embodiment all steps are performed aseptically so that the final product is sterile and consists of renatured tropocollagen. In a preferred embodiment the formulation is sterile.

As discussed herein and as will now be apparent to those of skill in the art based on the teachings and examples of the present invention, tropocollagen colloids and formulations thereof having the attributes of various embodiments of the present invention can be prepared from a variety of sources and using a variety of preparation methods. An illustrative method of preparing a tropocollagen formulation according to the present invention comprises the following steps: (i) a collagen grindate is denatured and solubilized in a first solution resulting in a solubilized collagen in solution, (ii) a renaturing agent is added to the solubilized collagen in solution resulting in the formation of renatured tropocollagen, (iii) the renatured tropocollagen is dispersed in a pharmaceutically acceptable excipient. In a preferred embodiment, the first solution is an acidic solution comprising pepsin, and the renaturing agent is a base added to the solution to increase the pH to neutral range and the solution is mixed to allow renatured tropocollagen to form. The renatured tropocollagen can then be isolated from the solution by centrifugation before being dispersed in a pharmaceutically acceptable excipient. In a preferred embodiment, the collagen grindate is obtained from bovine hides that have been soaked in an acidic solution. Preferably, the collagen in solution is passed through a sterile filter to remove contaminants and all subsequent steps are performed aseptically. In an illustrative embodiment of a tropocollagen colloid of the present invention, the tropocollagen formulation is approximately 2.6% bovine atelopeptide tropocollagen in the form of a selectively flowable sol. The sol can then be used to sterile fill devices such as syringe barrels comprising a reservoir adapted to contain the tropocollagen formulation and maintain it in sterile form. The syringe barrel is preferably adapted to receive an applicator tip suitable for application to the wound. In a preferred embodiment, the applicator tip is a flexible tube and the tropocollagen formulation can be extruded through the tube and onto the surface of a wound by applying hand pressure to a plunger operably linked to the syringe barrel.

In a preferred embodiment said kit includes an applicator tip for each syringe. In a preferred embodiment the applicator tip is for single use and is discarded after administration of the formulation.

In relation to the use of the formulation in the treatment of chronic wounds or ulcers, debridement and cleaning or the wound or ulcer is important. Cleaning and/or debridement of wounds or ulcers is necessary to remove necrotic tissue and pathogenic agents from the wound cite was well as to allow blood to flow into the wound for the healing process and, additionally, the formulation works in conjunction with platelets from fresh blood in the wound. Debridement of necrotic tissue for use in the method of the invention is preferably mechanical or surgical and performed in such a way that a small amount of blood is allowed to flow into the wound. When the wound has been subjected to debridement, the formulation may be applied either directly on or into the wound. Thus, the present invention relates also to the use of a debridement method in combination with the use of the formulation for the healing of wounds. The method of the invention includes the following two steps, namely i) a debridement method and ii) application of an formulation to the wound site. These steps can be repeated as necessary but preferably the wound will be debrided and the formulation applied no more than once a week. In a more preferred embodiment of the method of the invention, the wound will be debrided and the formulation applied no more than once every two weeks.

The invention further provides a kit which includes at least one applicator containing the formulation in an amount sufficient for at least one administration. In a preferred embodiment the kit includes an applicator tip.

EXAMPLES

The following examples are provided to further assist those of ordinary skill in the art. Such examples are intended to be illustrative and therefore should not be regarded as limiting the invention. A number of exemplary modifications and variations are described in this application and others will become apparent to those of skill in this art. Such variations are considered to fall within the scope of the invention as described and claimed herein.

Example 1

The hide of a bovine calf between 14 and 20 months old was mechanically ground and then soaked in acetic acid. The grindate was then removed from the acetic acid and soaked in an acidic solution (pH 2) containing pepsin to remove the telopeptides and to solubilize the collagen. The collagen was then purified and soaked in hydrochloric acid and filtered through a 0.2 micron sterile filter to remove contaminates. The sterile solubilized collagen was then placed in a sterile neutralization buffer and the tropocollagen was allowed to renature and stabilize. The collagen was then centrifuged and the precipitated pellet dispersed in a 6.5% PBS solution to produce a renatured tropocollagen sol. An MMP inhibitor, an antimicrobial agent, and a physiologically acceptable fluid were then added to the sol. This resulting colloid comprised approximately about 2.6% atelopeptide renatured tropocollagen.

Example 2

As an illustrative embodiment a formulation of the present invention prepared according to Example 1 was shown to effectively stimulate PDGF release from platelets. Even though the embodiment of the formulation did not comprise any PDGF or nucleic acid expressing PDGF or any vector comprising a nucleic acid expressing PDGF, this formulation was shown to be effective at eliciting the release of endogenous PDGF from platelets, and promoting wound healing.

Six clotting tubes were set-up in duplicate for testing activation of a commercially available platelet concentrate with Thrombin (as a positive control), the formulation prepared according to example 1 and a PBS as a negative control. Reconstituted platelet concentrate was placed into all six tubes. Two tubes received the positive control, Thombrin, two tubes received PBS, and two tubes received the formulation prepared according to example 1. Tubes were allowed to clot at 37° C.

Samples were removed from the tubes at six hours and twelve hours. The samples were centrifuged at 10,000×g for 10 minutes. Following centrifugation the supernatants were transferred to an appropriate container and frozen at −80° C. until the time of the assay. Qualitative analysis was performed by assessing secreted PDGF NB from the clotting mixture using a commercially available PDGF NB ELISA kit. Samples from the tubes treated with the formulation contained 7255 pg/ml of PDGF-AB after six hours and 16678 pg/ml of PDGF-AB after twelve hours. By comparison, the negative control had 4417 pg/ml of PDGF-AB after six hours and 5645 of PDGF-AB after twelve hours. This is a difference of 65% after six hours and 200% after twelve hours. This surprising and unexpected result demonstrates the ability of the formulation to stimulate the release of PDGF.

Example 3

As a further illustrative embodiment, a formulation of the present invention prepared according to Example 1 was shown to effectively stimulate PDGF release from platelets.

Clotting tubes for testing activation of a commercially available platelet concentrate were prepared with concentrations of 300 microliters or 720 microliters of the formulation prepared according to example 1 or PBS as a negative control. The tubes were allowed to clot at 37° C.

Samples were removed from the tubes at twenty-four and forty-eight hours. The samples were centrifuged at 10,000×g for 10 minutes at 4° C. Following centrifugation the supernatants were transferred to an appropriate container and frozen at −80° C. until the time of the assay. Qualitative analysis was performed by assessing secreted PDGF NB from the clotting mixture using a commercially available PDGF NB ELISA kit. After twenty-four hours, the tube containing a concentration or 300 microliters of the formulation was found to have 230% more PDGF than the negative control, while the tube containing a concentration of 720 microliters of the formulation was found to have over 300% more PDGF than the negative control. After forty-eight hours, the sample containing a concentration of 300 microliters of the formulation was found to have approximately 170% more PDGF than the negative control, while the sample containing a concentration of 720 microliters of the formulation was found to have over 200% more PDGF than the negative control. This result demonstrates the ability of the formulation to stimulate the release of PDGF.

Example 4

Forty eight human patients diagnosed with chronic ulcers (unhealed for at least 6 weeks), peripheral neuropathy (inability to perceive 10 g pressure using a Semmes-Weinstein 5.07 monofilament in the pert-ulcer area) and adequate blood flow (TcpO2>40 mmHg or a toe pressure>40 mmHg) were randomized into two groups. One group was treated with the Standard of Care (SOC) and the second group was treated with a tropocollagen formulation prepared according to Example 1 (FCG).

Following qualification and informed consent, patients underwent surgical debridement of the ulcer, biopsy for culture, ulcer photograph, and ulcer size measurement on Day-14 to start a screening 2-week Run-in period with SOC treatment. During the two week run-in period, all patients underwent surgical debridement to remove all necrotic soft tissue, hyperkeratotic wound margins, bacterial burden, cellular debris, sinus tracts, fistulae, undermined borders, and callus to produce viable wound margins and a clean ulcer site. If debridement was not necessary then the ulcer site and margins were lightly scored to create a small influx of blood into the wound site. All patients wore a special off-loading orthopedic shoe (DH Walker; Ossur, Coconut Creek, Fla.) during the Run-in period and throughout the trial.

The Day 1 visit consisted of surgical debridement of the ulcer if medically necessary, clinical assessment of the ulcer site and a photograph of the ulcer. The prepared fibrillar tropocollagen matrix was administered to patients randomized to the FCG group by application of 1 mL of the formulation per each 1 cm2 of the ulcer area. The formulation was applied as a continuous film over the entire ulcer area, including the margins. of the wound. The wound was covered and left undisturbed for one week. Patients randomized to the SOC group continued with daily dressing changes.

Primary patient data was wound photographs with rulers included for calibration and were taken from the same distance by means of a fixed focal length camera. Five blinded observers experienced or trained in wound evaluation independently traced all photographs to measure wound size from Day −14 through Week 2. Areas for a few problematic photographs were determined by group consensus.

Analysis of patient data demonstrated improved wound healing for the FCG group when compared with SOC group. Wounds in FCG group during Week 1 decreased on average by 1.97 mm2 compared to 0.78 mm2 in the SOC group, a result with a p value of less than 0.001. During Week 2, wounds in the FCG group decreased in radius 0.81 mm2 compared to 0.48 mm2 in the SOC group, a result with a p value of less than 0.01. This result and the degree of improvement in wound healing observed with a tropocollagen formulation of the present invention was both surprising and unexpected.

The invention claimed is:

1. A method to repair a wound by promoting platelet-derived growth factor (PDGF) release by platelets entering an in situ microstructural fibrillar matrix established in the wound, the method comprising the steps:
   (a) removing any necrotic tissue or pathogenic agents from the wound;
   debriding the wound to allow blood flow into the wound;
   (c) forming a permeable microstructural fibrillar matrix to act as an in situ scaffold for migration of cells by administering a formulation comprising a stabilized renatured atelopeptide tropocollagen as a continuous film over the wound area including margins of the wound, wherein the renatured atelopeptide tropocollagen promotes platelet activation and PDGF release,
   wherein the renatured atelopeptide tropocollagen is present at a concentration between 2.6% (w/v) and 10% (w/v) in the formulation,
   and wherein the renatured atelopeptide tropocollagen is stabilized by a polyol stabilizer to maintain microstructural integrity of the in situ microstructural fibrillar matrix formed in the wound; and
   (d) maintaining the microstructural fibrillar matrix in the wound for a period of time until cell migration occurs along and into both the margins and an interior surface of the wound, wherein the organization of growing repair tissue is regulated by the microstructure of the fibrillar matrix.

2. The method according to claim 1, wherein the renatured atelopeptide tropocollagen increases the activation of platelets to release PDGF by at least 50%.

3. The method according to claim 1, wherein the wound is selected from the group consisting of a traumatic injury wound, a diseased state, an iatrogenic wound, a soft tissue wound, a chronic wound and combinations thereof.

4. The method according to claim 3, wherein the wound is a chronic wound.

5. The method according to claim 4, wherein the chronic wound is a diabetic ulcer.

6. The method according to claim 5, wherein the diabetic ulcer is a diabetic foot ulcer.

7. The method according to claim 1, wherein the renatured atelopeptide tropocollagen in the formulation is not cross-linked.

8. The method according to claim 1, wherein the maintaining step comprises leaving the wound undisturbed for at least one week.

9. The method according to claim 1, wherein the renatured atelopeptide tropocollagen is present at a concentration of 2.6% (w/v) in the formulation.

10. The method according to claim 1, wherein the formulation further comprises a buffer.

11. The method according to claim 10, wherein the buffer is phosphate-buffered saline (PBS).

12. The method according to claim 1, wherein the polyol stabilizer is glycerol.

13. The method according to claim 1, wherein the formulation further comprises a solvent.

14. The method according to claim 1, wherein the formulation further comprises an antimicrobial agent.

15. The method according to claim 1, wherein the formulation further comprises a matrix metalloproteinase (MMP) inhibitor.

16. The method according to claim 15, wherein the MMP inhibitor is a zinc chelating agent.

17. The method according to claim 1, wherein the renatured atelopeptide tropocollagen is derived from bovine type I collagen.

18. The method according to claim 1, wherein the formulation further comprises a wound-healing agent.

19. The method according to claim 18, wherein the wound-healing agent is selected from the group consisting of:
   agents that promote the endogenous production of nitric oxide by endothelial cells;
   monoclonal antibodies directed against surface markers of progenitor endothelial cells;
   wound-healing cells;
   extracellular matrix proteins;
   anti-inflammatory agents;
   vitamin A;
   lipid peroxidation inhibitors;
   neovascularization and angiogenesis promoters;
   procollagen expression promoters;
   glucocorticoid receptor antagonists;
   and combinations thereof.

20. The method according to claim 19, wherein the wound-healing agent is a glucocorticoid receptor antagonist.

21. The method according to claim 20, wherein the glucocorticoid receptor antagonist is a steroidal antiglucocorticoid.

22. The method according to claim 18, wherein the wound-healing agent is selected from the group consisting of insulin, erythropoietin, interferons, protein C, hirudin, granulate-macrophage colony-stimulating factor, somatotropin, epidermal growth factor, albumin, hemoglobin, lactoferrin, angiotensin-converting enzyme, glucocerebrosidase, human growth hormone, vascular endothelial growth factor (VEGF), antibodies, and combinations thereof.

23. The method according to claim 1, wherein the formulation further comprises a saline solution.

* * * * *